(12) United States Patent
Ochoa Velez et al.

(10) Patent No.: US 11,547,582 B2
(45) Date of Patent: Jan. 10, 2023

(54) LOWER LIMB PROSTHESIS

(71) Applicant: BLATCHFORD PRODUCTS LIMITED, Basingstoke (GB)

(72) Inventors: Juan Jose Ochoa Velez, Medellin (CO); Mir Saeed Zahedi, London (GB); Robert Michael Andrew Painter, Basingstoke (GB)

(73) Assignee: Blatchford Products Limited, Hampshire (GB)

( * ) Notice: Subject to any disclaimer, the term of this patent is extended or adjusted under 35 U.S.C. 154(b) by 0 days.

(21) Appl. No.: 16/542,888

(22) Filed: Aug. 16, 2019

(65) Prior Publication Data
US 2020/0054465 A1 Feb. 20, 2020

(30) Foreign Application Priority Data
Aug. 17, 2018 (GB) ..................... 1813443

(51) Int. Cl.
*A61F 2/64* (2006.01)
*A61F 2/66* (2006.01)
(Continued)

(52) U.S. Cl.
CPC ............ *A61F 2/644* (2013.01); *A61F 2/6607* (2013.01); *A61F 2/70* (2013.01); *A61F 2/74* (2021.08);
(Continued)

(58) Field of Classification Search
CPC .......... A61F 2/644; A61F 2/6607; A61F 2/70; A61F 2/64; A61F 2002/607; A61F 2002/6614; A61F 2002/701; A61F 2002/704; A61F 2002/745; A61F 2002/747; A61F 2002/748
See application file for complete search history.

(56) References Cited

U.S. PATENT DOCUMENTS 5,893,891 A 4/1999 Zahedi
6,517,585 B1 2/2003 Zahedi et al.
(Continued)

FOREIGN PATENT DOCUMENTS

GB 2270473 A 3/1994
WO WO 2012/166853 A1 12/2012

OTHER PUBLICATIONS

Search Report for Great Britain Application No. GB 1813443.7 dated Feb. 17, 2019.
(Continued)

*Primary Examiner* — Jerrah Edwards
*Assistant Examiner* — Aren Patel
(74) *Attorney, Agent, or Firm* — Alston & Bird LLP

(57) ABSTRACT

A lower limb prosthesis comprises a knee chassis (10), a shin carrier (20) pivotally connected to the knee chassis (10) and a piston and cylinder assembly (30, 40) pivotally connected to the knee chassis (10) and the shin carrier (20). The piston and cylinder assembly (30, 40) comprises a piston assembly (40) comprising a piston (40) mounted on a piston rod (42), a cylinder body (32B) having a cavity (46) defining a cylinder within which the piston (44) is arranged to reciprocate along the piston and cylinder assembly axis, and a foot component attachment means (36) for attaching a foot component to the piston and cylinder assembly (30, 40).

20 Claims, 15 Drawing Sheets

(51) Int. Cl.
  *A61F 2/70* (2006.01)
  *A61F 2/50* (2006.01)
  *A61F 2/60* (2006.01)
  *A61F 2/74* (2006.01)
(52) U.S. Cl.
  CPC ....... *A61F 2/748* (2021.08); *A61F 2002/5038* (2013.01); *A61F 2002/607* (2013.01); *A61F 2002/6614* (2013.01); *A61F 2002/701* (2013.01); *A61F 2002/704* (2013.01)

(56) References Cited

U.S. PATENT DOCUMENTS

| | | | |
|---|---|---|---|
| 6,706,074 B1* | 3/2004 | Chen | A61F 2/68 623/44 |
| 6,719,806 B1 | 4/2004 | Zahedi et al. | |
| 8,313,534 B1 | 11/2012 | Chen et al. | |
| 2004/0181289 A1* | 9/2004 | Bedard | A61F 2/66 623/24 |
| 2007/0083272 A1 | 4/2007 | Van De Veen et al. | |
| 2008/0262635 A1 | 10/2008 | Moser et al. | |
| 2008/0281435 A1* | 11/2008 | Abimosleh | A61F 2/6607 623/50 |
| 2009/0187260 A1 | 7/2009 | Steiner et al. | |
| 2010/0185301 A1* | 7/2010 | Hansen | A61F 2/6607 623/47 |
| 2011/0098828 A1* | 4/2011 | Balboni | A61F 2/60 623/40 |
| 2012/0330440 A1 | 12/2012 | Chen et al. | |
| 2013/0173019 A1* | 7/2013 | Sykes | A61B 5/4851 623/24 |
| 2016/0324665 A1* | 11/2016 | Boiten | A61F 2/644 |
| 2018/0098864 A1* | 4/2018 | Auberger | A61F 2/64 |

OTHER PUBLICATIONS

Kothival, K. et al., *Anthropometry for Design for the Elderly*, International Journal of Occupational Safety and Ergonomics 2001, vol. 7, No. 1 (Jan. 2015) 15-34.
Extended European Search Report for EP No. 19191137.9 dated Jul. 31, 2020 (10 pages).
Examination Report for British Application No. GB1813443.7 dated Aug. 24, 2022 (4 pages).
U.K. Examination Report for Application No. GB1813443.7 dated Jan. 26, 2022 (6 pages).

* cited by examiner

LOWER LIMB PROSTHESIS

CROSS REFERENCE TO RELATED APPLICATIONS

This application claims priority to United Kingdom Application No. GB 1813443.7, filed Aug. 17, 2018, the entire contents of which are incorporated herein by reference.

TECHNICAL FIELD

The present invention relates to a lower limb prosthesis. In particular, the present invention relates to a knee prosthesis having a polycentric linkage.

BACKGROUND

A person skilled in the art will appreciate that walking involves what is known as a "gait cycle". A gait cycle comprises a stance phase (during which weight is transferred through the leg), and a swing phase (in which the leg is swung forwards, and does not support the weight of the body).

Lower limb prostheses are used to restore an amputee's ability to walk, by supporting the weight of an amputee, for example during a stance phase of their gait cycle when walking or running, or when standing.

In a known lower limb prosthesis, the mechanical joint includes a linear or a rotary control unit. The linear control unit consists of a piston running inside a cylinder, and has an advantage compared to the rotary control in that it is easier to apply seals in this configuration than in a rotary embodiment.

A known linearly controlled knee prosthesis is the single axis prosthesis, which has a fixed instantaneous centre of rotation (ICR) of relative motion between the femur and the shank. Another knee prosthesis is a polycentric prosthesis, in which the position of the ICR changes at each flexion angle. An example of a polycentric prosthesis is the four-bar, four-pivot (i.e., four revolute joint) mechanism prosthesis.

The term "four bar prosthesis" is typically used to refer to 4-bar, 4-revolute joints in polycentric linkages. However, a monocentric configuration having a piston and cylinder (i.e., wherein there are three revolute joints and one sliding joint) may also be referred to as a four-bar configuration. There have been various developments related to lower limb prostheses (specifically four-bar prostheses having three revolute joints and one sliding joint), several of which will be described below.

In one known monocentric lower limb prosthesis sold under the brand name Mercury® made by Blatchford Products Limited, the lower limb prosthesis has a thigh component, a shin component and a knee pivot disposed between those components forming a knee joint. The shin component houses a piston and cylinder assembly having a cylinder which is mounted to the shin component by a cylinder mounting pivot, and a piston which is mounted to the thigh component by a piston mounting pivot offset to the posterior of the knee pivot. The piston and cylinder assembly acts as a knee flexion and extension control unit in order to control the flexion and extension of the knee joint so as to allow walking. When the knee is flexed, the piston is pushed further into the cylinder, and when it is straightened, the piston is withdrawn from the cylinder. In this way, the piston and cylinder assembly itself forms a sliding joint.

As a person skilled in the art will appreciate, during the swing phase of the gait cycle the foot is raised above the ground. As the thigh component progresses forward, the shin component swings forward to extend the knee until the leg is straight. The piston and cylinder assembly permits lightly damped movement of the knee joint during this phase, but once the shin component is fully extended, the knee is substantially locked so that the shin component is retained in the extended position so as to support the weight of the amputee as the amputee moves forward to stand on the prosthesis, thereby entering the stance phase. Generally, the piston and cylinder assembly yields to a limited degree during the stance phase to make it easier to walk down a slope, or down steps, and to sit down.

During the stance phase, following heel strike, the amputee continues to move forwards over the foot until his/her weight is borne wholly on the front of the foot. This creates a hyperextension moment around the knee joint of the Mercury® lower limb prosthesis, tending to make the knee as straight as possible. The hyperextension moment can be enhanced by the amputee intentionally moving his thigh backwards when his weight is wholly borne on the front of the foot. The piston and cylinder assembly can be designed such that the hyperextension moment can be used to release the lock from the knee joint to permit the knee joint to flex in a final part of the stance phase. As the toe leaves the ground, the shin component continues to turn about the flexing knee joint with respect to the thigh component and the thigh component moves forward thereby entering the swing phase once again.

The piston and cylinder assembly includes a number of valves which open and close according to the phase of the gait cycle that is occurring at each instance. During the stance phase, the piston is at its maximum extension from the cylinder, corresponding to extension of the knee joint.

US patent application published as US 2009/0187260 A1 describes a lower limb prosthesis having a monocentric mechanism, the monocentric mechanism comprising a piston and cylinder assembly. The piston and cylinder assembly of this lower limb prosthesis is intended to oppose a predetermined resistance during flexion, the resistance being switched between a predetermined minimal and a predetermined maximal value.

U.S. Pat. No. 5,893,891, the contents of which are incorporated herein by reference, describes a prosthesis control system, in which optimal prosthesis movement is recorded during a "teach mode" and applied during use of the prosthesis through optimised valve opening control.

U.S. Pat. No. 6,517,585 B1, the contents of which are incorporated herein by reference, describes a lower limb prosthesis in which flexion at the knee joint is resisted by means of a dual piston and cylinder assembly. Sensors are used to sense knee bending moments and knee flexion angle. This information is used to adjust hydraulic and pneumatic resistance depending on whether, for example, the amputee is running or walking. The system is configured so that hydraulic resistance predominates during a stance phase, and pneumatic resistance predominates during a swing phase. Programmable resistance allows a tailored response depending on whether the amputee is walking on a flat surface, or on an incline, walking down stairs, or during a fall.

U.S. Pat. No. 6,719,806 B1, the contents of which are incorporated herein by reference, also describes a lower limb prosthesis. In this patent, the lower limb prosthesis includes a dynamically adjustable knee movement control unit, which allows for flexion control in response to a step-to-step variability of a kinetic or kinematic parameter of movement (such as the amplitude of the flexion angle of the joint), in order to reduce the step-to-step variability.

US patent application published as US 2013/0173019 A1, the contents of which are incorporated herein by reference, describes a self-teaching lower limb prosthesis, having a dynamically adjustable joint movement control unit. The control unit stores a target relationship between a kinetic or kinematic parameter of locomotion and walking speed, and generates monitoring signals representative of walking speed values, and values of the parameter occurring at different walking speeds. The self-teaching lower limb prosthesis further comprises an adjustment system which adjusts the control unit automatically when the monitoring signals show a deviation from the target relationship, to bring the parameters close to that defined by the target relationship.

US patent application published as US 2007/0083272 A1 describes a prosthetic knee joint having a four-bar linkage (three revolute joints and one sliding joint). The teaching in this document includes locking of the prosthesis during standing and walking in order to ensure safety for a geriatric patient. A further description of an embodiment of this document is described below in relation to FIG. 1B.

Referring to FIG. 1A, there is provided a prior art monocentric mechanism stabilising lower limb prosthesis incorporating part of a control system, as described and shown in U.S. Pat. No. 5,893,891, referred to above. This prior art prosthesis has a knee joint 10' with a knee pivot 12' connecting a thigh component 14' to a shin component 16'. The thigh component 14' comprises a knee chassis 14A', an alignment device 14B', and a residuum socket 14C' (partially shown in the Figure). The shin component 16' has a conventional carbon fibre reinforced plastics shin cradle 16A' which houses a piston and cylinder assembly 18' acting as a flexion control device. The assembly 18' comprises a cylinder 18A' which is pivotally coupled to the posterior part of the shin cradle 16A' and a piston 18B' having a piston rod 18C' which is pivotally coupled to the knee chassis 14A'. Pivotal coupling 21' connects the cylinder 18' to the shin 16'. The piston and cylinder assembly 18' is a pneumatic device, the resistance to flexion of the knee joint 10' being controlled by a needle valve 18D' which is adjustable by an electrical stepper motor 20' and an associated screw-threaded shaft 20A' connected to the needle member of the needle valve 18D'. The needle valve 18D' lies in a passage 18E' in the body of the cylinder 18A', the passage 18E' interconnecting the cylinder interior spaces 18F', 18G' on opposite sides of the piston 18B', the passage 18E' emerging at a port 18H' in the wall of the cylinder 18A'. Operation of the motor 20' causes the shaft 20A' to move axially so that the needle member moves into or out of a passageway forming part of the passage 18E'.

The passage 18E' constitutes a first bypass passage interconnecting the cylinder spaces 18F', 18G' on opposite sides of the piston 18B'. A second bypass passage 18I' incorporating a valve such as a one-way valve 18J' is formed in the piston 18B' so that the needle valve 18D' is effective only on one stroke of the piston, in this case the stroke corresponding to increasing flexion of the knee joint 10'. The one-way valve 18J' may be arranged so as not to close-off the second bypass passage 18I' completely on the increasing flexion stroke, but rather merely to reduce the orifice area through the piston 18B'. Such an arrangement has the effect of the needle valve 18D' determining the resistance to motion of the piston 18B' in both directions, i.e., for increasing and decreasing flexion, but with the effect of variations in the orifice area of the needle valve 18D' being greater in one direction than the other, depending on the direction of operation of the valve 18J'.

The stepper motor 20' is driven by the combination of a microcomputer and receiver which together form assembly 22'. The microcomputer determines knee flexion and extension movements by means of a magnetic proximity sensor, preferably a transducer 24A', mounted in or associated with the cylinder 18A', and a permanent magnet 24B' mounted on or associated with the piston 18B'. The electronic circuitry 22' and the stepper motor 20' are powered by batteries, one of which is shown in FIG. 1A and indicated by the reference 26'.

A schematic of the linkage arrangement of the prior art device of FIG. 1A is shown in FIG. 2. The prior art linkage arrangement comprises a knee chassis link 110', a shin carrier link 120', a cylinder body link 130', and a piston rod assembly link 140'. In relation to FIG. 1A, knee chassis link 110' corresponds to knee chassis 14A'; shin carrier link 120' corresponds to shin cradle 16A'; cylinder body link 130' corresponds to cylinder 18A'; and piston rod assembly link 140' corresponds to piston rod 18C'.

As shown in the schematic in FIG. 2, the knee chassis link 110' is pivotally connected to the shin carrier link 120' at pivot point or axis A'. The shin carrier link 120' is pivotally connected to the cylinder body link 130' at pivot point or axis B'. The cylinder body link 130' is translationally connected to the piston rod assembly link 140'. The piston rod assembly link 140' is pivotally connected to the knee chassis link 110' at pivot point or axis C'. Pivot point B' is proximate, but not at, a distal end 124' of the shin carrier link 120'. Distal end 124' of the shin carrier link 120' is to be connected to a shank and/or a foot prosthesis (not shown).

FIG. 1B is a representation of a prior art prosthesis described in US patent publication US 2007/0083272 A1, referred to above. As described in this US patent application, the prosthesis has an upper part 10" and a lower part 20", the upper part 10" and the lower part 20" being connected pivotally to one another via an articulation device. This articulation device comprises a front articulation lever 40" which is secured rotatably both on the upper part 10" and also on the lower part 20". A resistance device 30", which is designed as a hydraulic cylinder device, prevents an uncontrolled flexion movement of the lower part 20" relative to the upper part 10" counter to the normal walking direction, that is to say a forwardly directed walking direction. The configuration of the articulation device has the effect that a large part of the load which arises during walking or standing, and which is exerted on the prosthetic knee joint by the prosthesis user, is introduced via the resistance device 30" into the lower part 20" and from there into a shin portion 200". At the upper end of the upper part 10" there is a socket 100" for receiving the thigh residuum. The prosthetic knee joint further comprises a knee cap 50" which is arranged on the front articulation lever 40" (and which is referred to in the patent application as an "operating device").

A schematic of the linkage arrangement of the prior art device of FIG. 1B is shown in FIG. 20A and FIGS. 21A, 22A and 23A.

Comparing this prior art prosthesis to the schematic representation of FIG. 2, FIG. 20A shows that the linkage arrangement comprises a knee chassis link 110", a shin carrier link 120", a cylinder body link 130", and a piston rod assembly link 140". Knee chassis link 110" corresponds to upper part link 10" of FIG. 1B; shin carrier link 120" corresponds to front articulation lever link 40"; cylinder body link 130" corresponds to an upper part of lower part link 20"; and piston rod assembly link 140" corresponds to resistance device link 30". Cylinder body link 130" comprises a cylinder body arm 131", on which pivot point B" is located.

As shown in the schematic in FIG. 20A, the knee chassis link 110" is pivotally connected to the shin carrier link 120" at pivot point or axis A". The shin carrier link 120" is pivotally connected to the cylinder body link 130" at pivot point or axis B". The cylinder body link 130" is translationally connected to the piston rod assembly link 140". The piston rod assembly link 140" is pivotally connected to the knee chassis link 110" at pivot point or axis C". Pivot point B" is distal to the shin carrier link 120" relative to the pivot point A".

FIGS. 21A, 22A and 23A show schematic illustrations of rotation of the device of FIG. 1B, in which the instantaneous centre of rotation is marked as 91".

STATEMENTS OF INVENTION

According to a first aspect of the invention there is provided a lower limb prosthesis, comprising:
a knee chassis;
a shin carrier pivotally connected to the knee chassis; and
a piston and cylinder assembly pivotally connected to the knee chassis and the shin carrier, the piston and cylinder assembly comprising:
    a piston assembly comprising a piston mounted on a piston rod; and
    a cylinder body having a cavity defining a cylinder within which the piston is arranged to reciprocate;
wherein:
the knee chassis is pivotally connected to the shin carrier to pivot around an anterior knee pivot axis (A);
the knee chassis is pivotally connected to the piston and cylinder assembly to pivot around a posterior knee pivot axis (C); and
the shin carrier is pivotally connected to the piston and cylinder assembly to pivot around a distal pivot axis (B),
wherein the piston and cylinder assembly further comprises, distal to the distal pivot point (B), a foot component having a lower surface, and a distance from the anterior knee pivot axis (A) to the distal pivot axis (B) is more that 20% of a distance from the anterior knee pivot axis (A) to the lower surface of the foot component, or
the piston and cylinder assembly further comprises, distal to the distal pivot point (B), attachment means for attaching a foot component to the piston and cylinder assembly, said foot component having a lower surface, and, in use, when said foot component is attached to the attachment means a distance from the anterior knee pivot axis (A) to the distal pivot axis (B) is more that 20% of a distance from the anterior knee pivot axis (A) to the lower surface of said foot component.

The distance between the anterior knee pivot axis (A) and the distal pivot axis (B) may be more than 20%, 25%, 30%, 35%, 40% or 45% of the distance from the anterior knee pivot axis (A) to the lower surface of the foot, depending on the height of the amputee.

According to a second aspect of the invention there is provided a lower limb prosthesis, comprising:
a knee chassis;
a shin carrier pivotally connected to the knee chassis; and
a piston and cylinder assembly pivotally connected to the knee chassis and the shin carrier and having a piston and cylinder assembly axis, the piston and cylinder assembly comprising:
    a piston assembly comprising a piston mounted on a piston rod;
    a cylinder body having a cavity defining a cylinder within which the piston is arranged to reciprocate along the piston and cylinder assembly axis; and
    a foot component or attachment means for attaching a foot component to the piston and cylinder assembly;
wherein:
the knee chassis is pivotally connected to the shin carrier to pivot around a first knee pivot axis (A);
the knee chassis is pivotally connected to the piston and cylinder assembly to pivot around a second knee pivot axis (C); and
the shin carrier is pivotally connected to the piston and cylinder assembly to pivot around a distal pivot axis (B),
the lower limb prosthesis having a centrode about which the prosthesis rotates, the instantaneous centre of rotation being a point where a line passing through the first knee pivot axis (A) and the distal pivot axis (B) intersects a line passing through the second knee pivot axis (B) and which is perpendicular to the piston and cylinder assembly axis,
wherein when the piston reciprocates within the cylinder the instantaneous centre of rotation of the lower limb prosthesis follows a centrode twice intersecting a line passing through the second knee pivot axis (A) and the second knee pivot axis (C).

When the piston reciprocates within the cylinder the centrode substantially defines a semi-circle circumference or two thirds of a circle circumference.

According to a third aspect of the invention there is provided a lower limb prosthesis, comprising:
a knee chassis;
a shin carrier pivotally connected to the knee chassis; and
a piston and cylinder assembly pivotally connected to the knee chassis and the shin carrier and having a piston and cylinder assembly axis, the piston and cylinder assembly comprising:
    a piston assembly comprising a piston mounted on a piston rod;
    a cylinder body having a cavity defining a cylinder within which the piston is arranged to reciprocate along the piston and cylinder assembly axis; and
    a foot component or attachment means for attaching a foot component to the piston and cylinder assembly;
wherein:
the knee chassis is pivotally connected to the shin carrier to pivot around an anterior knee pivot axis (A);
the knee chassis is pivotally connected to the piston and cylinder assembly to pivot around a posterior knee pivot axis (C); and
the shin carrier is pivotally connected to the piston and cylinder assembly to pivot around a distal pivot axis (B),
wherein the piston and cylinder assembly axis and a line passing through the anterior knee pivot axis (A) and the distal pivot axis (B) are substantially parallel as the knee flexes.

According to a further aspect of the invention there is provided a lower limb prosthesis, comprising:
a knee chassis;
a shin carrier pivotally connected to the knee chassis; and a piston and cylinder assembly pivotally connected to the knee chassis and the shin carrier and having a piston and cylinder assembly axis, the piston and cylinder assembly comprising:
- a piston assembly comprising a piston mounted on a piston rod;
- a cylinder body having a cavity defining a cylinder within which the piston is arranged to reciprocate along the piston and cylinder assembly axis; and
- a foot component or attachment means for attaching a foot component to the piston and cylinder assembly;

wherein:
- the knee chassis is pivotally connected to the shin carrier to pivot around an anterior knee pivot axis (A);
- the knee chassis is pivotally connected to the piston and cylinder assembly to pivot around a posterior knee pivot axis (C); and
- the shin carrier is pivotally connected to the piston and cylinder assembly to pivot around a distal pivot axis (B) which lies substantially on the piston and cylinder assembly axis.

Any of lower limb prostheses described above may further comprise control means configured to control relative movement between the cylinder body and the piston assembly The control means may be configured to control relative movement between the cylinder body and the piston assembly in dependence on the position of the prosthesis in a gait cycle.

The control means may be a hydraulic or pneumatic control means, comprising at least one electronically-controlled valve.

The control means may comprise a micro-processor, the micro-processor being comprised in or on the lower limb prosthesis.

The cylinder body may comprise a cylinder sleeve, the cylinder sleeve being configured to receive the piston such that translational movement of the piston within the cylinder sleeve is permitted, and the attachment means may be fixedly attached to or form part of the cylinder sleeve.

The foot component may be a shin, ankle or foot prosthesis.

The attachment means may be a pyramid connector.

The piston rod may defines an internal cavity.

The piston rod may have a distal end and a proximal end, the distance between the proximal end and the distal end defining a length, the internal cavity extending along at least half of the piston rod length.

The internal cavity of the piston rod may have a diameter of between 6 mm and 10 mm.

The internal cavity may define a cylinder and the lateral dimension may be a diameter of the cylinder defined by the internal cavity.

The internal cavity may have an open end and a closed end, the open end being open to the cylinder.

The piston rod may be a single unitary piece of titanium alloy.

The lower limb prosthesis may further comprise an adaptive control system having a flexion control device arranged to resist flexion at a knee joint hydraulically, and an electronic processing circuit electrically coupled to sensor means, and a control device for automatically adjusting the hydraulic resistance to knee flexion according to actions of the user.

The lower limb prosthesis may further comprise a microprocessor for controlling knee flexion.

The lower limb prosthesis may further comprise at least one valve for flexion and/or extension control.

The lower limb prosthesis may further comprise a flexion flow control valve and an extension flow control valve.

The flexion flow control valve and the extension flow control valve may both be controlled by a single actuator, the actuator being controlled by micro-processor control.

BRIEF DESCRIPTION OF THE FIGURES

The present invention will now be described by way of example only, and with reference to the accompanying drawings in which:

FIGS. 21A and 21B to 23A and 23B are schematic representations of the prior art prosthesis of FIG. 20A, and the present prosthesis of FIG. 20B, arranged in first (21), second (22) and third (23) positions respectively.

DETAILED DESCRIPTION OF PREFERRED EMBODIMENTS

Figure 1A:
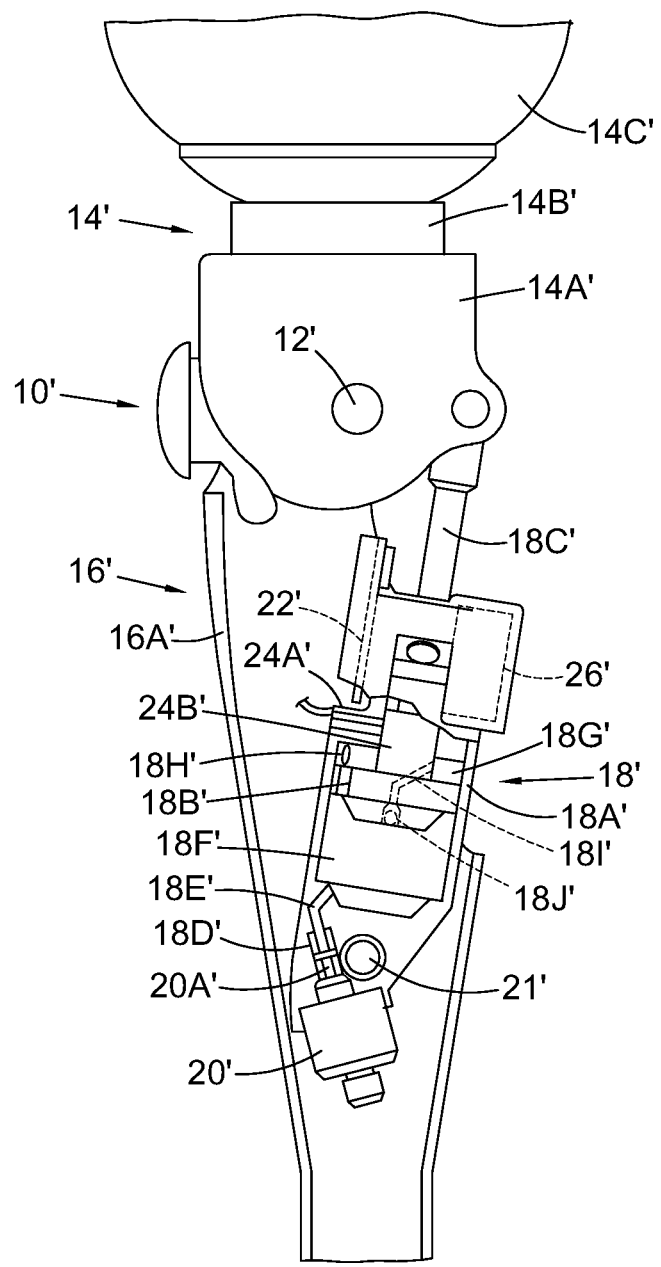
FIG. 1A is a partly sectioned side elevation of part of a first prior art lower limb prosthesis.
Figure 2:
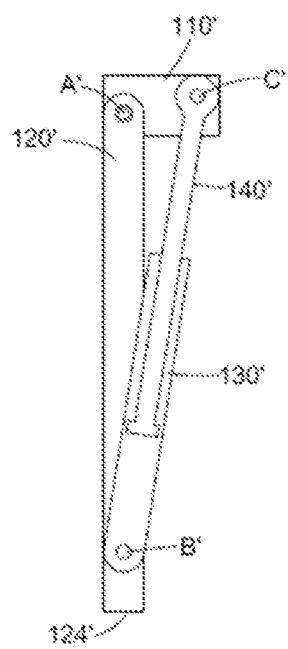
FIG. 2 is a schematic showing the linkage arrangement of the prior art device shown in FIG. 1A.

FIGS. 1A and 2, which depict a first prior art lower limb prosthesis, have been described above in the section "Background".

Figure 3:
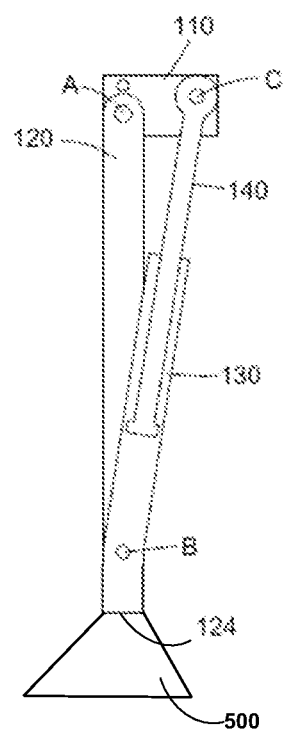
FIG. 3 is a schematic showing the linkage arrangement of a knee prosthesis in accordance with the invention.
Figure 4:
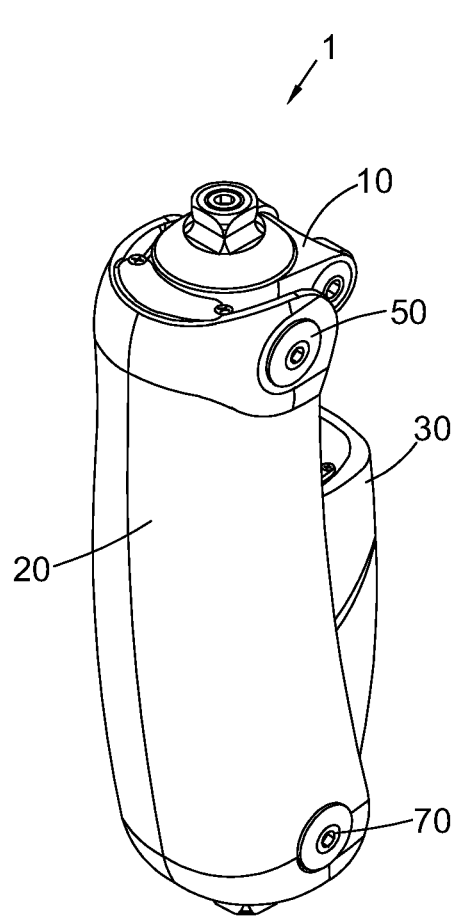
FIG. 4 is a front diagonal projection of a first embodiment of a knee prosthesis in accordance with the invention.
Figure 5:
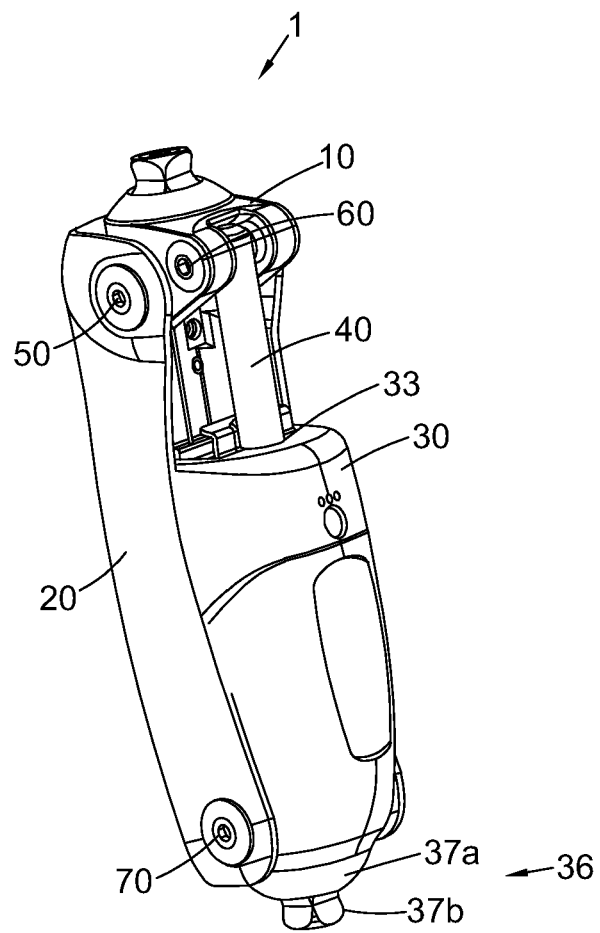
FIG. 5 is a rear diagonal projection of the embodiment shown in FIG. 4.
Figure 6:
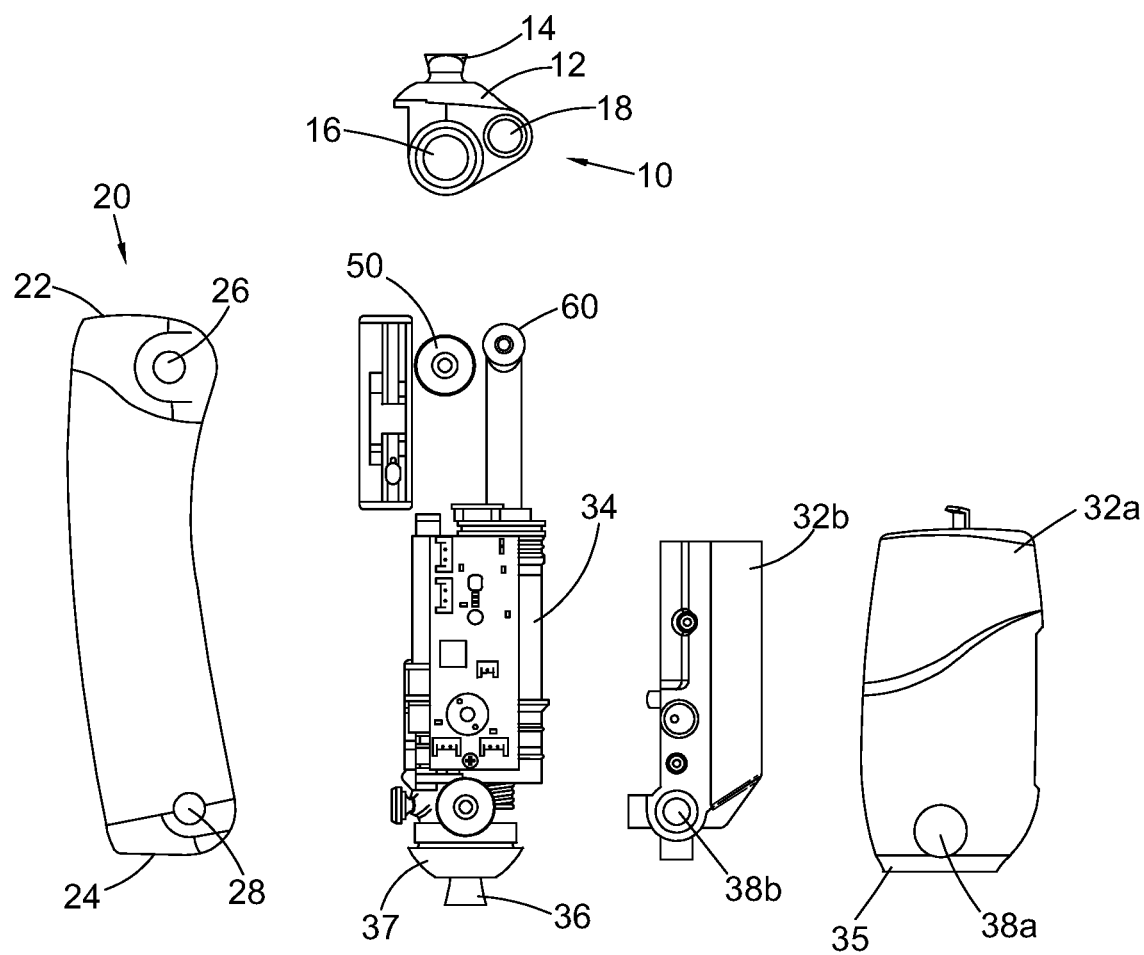
FIG. 6 is a partially exploded view of the embodiment shown in FIG. 4.

A schematic of the linkage arrangement of a first embodiment of the present knee prosthesis is shown in FIG. 3. As shown in FIG. 3, the linkage arrangement of the first embodiment of the knee prosthesis is similar to the prior art schematic in FIG. 2 in that it comprises a knee chassis link 110, a shin carrier link 120, a cylinder body link 130, and a piston rod assembly link 140. The knee chassis link 110 is pivotally connected to the shin carrier link 120 at pivot point A, which defines an anterior knee pivot axis. The shin carrier link 120 is pivotally connected to the cylinder body link 130 at pivot point or axis B, which defines a distal axis. The cylinder body link 130 is translationally connected to the piston rod assembly link 140. The piston rod assembly link 140 is pivotally connected to the knee chassis link 110 at pivot point C, which defines a posterior knee pivot axis.

The linkage arrangement of the first embodiment of the knee prosthesis is a polycentric arrangement. This differs from the linkage arrangement of the prior art schematic of FIG. 2 which is a monocentric arrangement.

The linkage arrangement of the first embodiment of the knee prosthesis differs from the prior art schematic of FIG. 2 in that a distal end 124 of the cylinder body link 130 is configured for attachment to a shank and/or an ankle/foot prosthesis (not shown). In order to facilitate this, pivot point B is proximate, but not at, the distal end 124 of the cylinder body link 130. The cylinder body link 130 is configured to extend beyond pivot point B where it is pivotally attached to the shin carrier link 120. This is in contrast to the prior art linkage arrangement shown in FIG. 2, in which the shin carrier link 120' is configured to extend beyond pivot point B' where it is pivotally attached to the cylinder body link 130'.

In addition, the pivot point B is at a distal end of the piston and cylinder assembly formed by the cylinder body link 130 and the piston rod assembly link 140 translational combination. As can be seen from FIG. 3, the combined length of the cylinder body link 130 and the piston rod assembly link 140 between pivot points B and C when the knee is extended is slightly greater than the length of the portion of the shin carrier link 120 extending between pivot points A and B. Furthermore, it is readily apparent from FIG. 3 that when the knee joint is flexed, leading to the shortening of the overall length of the cylinder body link 130 and the piston rod assembly link 140, the overall length of the cylinder body link 130 and the piston rod assembly link 140 between pivot points B and C reduces until it is less than the fixed length of the portion of the shin carrier link 120 extending between pivot points A and B. In other words, the distance from pivot point B to C varies between the distance from pivot point A to B+X % and the distance from pivot point A to B-Y %, where X may be of the order of Y and/or where X and Y may be 5, 10 and 15. For example, when the overall length of the cylinder body link 130 and the piston rod assembly link 140 is at its maximum (when the knee is fully extended) the distance from pivot point B to C may be 5% more than the distance from pivot point A to B and when the overall length of the cylinder body link 130 and the piston rod assembly link 140 is at its minimum (when the knee is fully flexed) the distance from pivot point B to C may be 20% less than the distance from pivot point A to B.

In addition, the distance between pivot points A and B is, in use, a significant portion of the height of the pivot point A above the base of a foot prosthesis (e.g., foot component 500) attached at the distal end 124 of the cylinder body link 130. In particular the distance between pivot points A and B may be at least 20%, 25%, 30%, 35%, 40% or 45% of the height of the pivot point A above the base of such a foot prosthesis, depending on the height of the amputee.

With reference to the linkage in FIG. 2, if the distal end 124' is considered fixed in space, the knee chassis link 110' rotates about an axis through the fixed pivot point A', which constitutes the knee axis. The knee axis is stationary and the knee joint is said to be monocentric. On the other hand, and with reference to the linkage in FIG. 3, if the distal end 124 is fixed in space, the pivot point C moves in a straight line following the axis of the cylinder body, while the pivot point A moves along an arc, the arc having its centre at the pivot point B. The movement of the knee chassis link 110 is then a combination of translation and rotation, in which the location of the instantaneous centre of rotation of the knee chassis link 110 relative to the distal end 124 changes continuously as the knee flexes. As indicated previously, a joint in which the instantaneous centre of rotation changes, such as in the configuration described above, is called a polycentric joint. In this context, the instantaneous centre of rotation of the knee joint is taken as the point where a line passing through the pivot points A and B crosses a line passing through pivot point C and which is perpendicular to the axis of the piston and cylinder assembly.

The linkage arrangement shown in FIG. 3 has several advantages when compared with the linkage in FIG. 2. Firstly, the cylinder and the distal end of the joint constituting a single body facilitates the integration of additional prosthetic components, which would normally be independent from the knee joint, such as linear or rotational dampers. This integration allows for a simpler, more compact, overall build height and simplified manufacture of the prosthetic joint. Secondly, if a means for controlling flexion resistance requires sensors for measuring bending moments in the distal end of the joint, such sensors (e.g. strain gauge or similar device) can be integrated into the cylinder body. This allows the sensor(s) to be proximate to other electrical components, allowing for simple wiring. Optionally, such sensors can be integrated together with the corresponding electronic circuit boards. Thirdly, integration of the cylinder and control components into a single body allows for a simpler design of a protective cover for the cylinder. Optionally, the protective cover can be dust-proof or water-proof. Fourthly, the polycentric nature of the prosthesis replicates actual movement in a human knee, in which the femur shifts posteriorly relative to the tibia as the knee flexes, allowing for a symmetric knee flexion when the amputee is sitting on a chair. A posterior shift is also achieved in the polycentric prostheses of the invention described herein.

The differences in linkage arrangements between the schematics in FIGS. 2 and 3 have significant structural consequences. In use, the prior art linkage arrangement of FIG. 2 isolates the cylinder body link 130' and the piston rod assembly link 140' from lateral forces and bending moments. However, in the present linkage arrangement of FIG. 3, the cylinder body link 130' and the piston rod assembly link 140' are both subject to lateral forces and bending moments in use. The schematic of FIG. 3 has several advantages. One advantage is that a strain gauge or similar device can be attached to the piston and cylinder assembly. This allows the strain gauge to be proximate to other electrical components, allowing for simple wiring. This also allows for a simpler, more compact device, in which electrical components are proximate to each other. Further advantages of the polycentric arrangement will be described later in relation to the first and second embodiments.

FIGS. 4 to 7 are views of the first embodiment of the knee prosthesis in accordance with the invention. The knee prosthesis 1 comprises: a knee chassis 10, a shin carrier 20, a cylinder assembly 30, piston rod assembly 40, a knee chassis pivot shaft (KCPS) 50, a piston rod pivot shaft (PRPS) 60, and a cylinder body pivot shaft (CBPS) 70. The knee chassis 10 corresponds to the knee chassis link 110 described above in relation to the schematic of FIG. 3. The shin carrier 20 corresponds to the shin carrier link 120; the cylinder assembly 30 corresponds to the cylinder body link 130; the piston rod assembly 40 corresponds to the piston rod assembly link 140; the KCPS 50 corresponds to pivot point A; the CBPS 70 corresponds to pivot point B; and the PRPS 60 corresponds to pivot point C of the schematic shown in FIG. 3. In the knee prosthesis 1 of FIGS. 4 to 7 the knee chassis 10 is dimensioned such that the distance between KCPS 50 pivot point A and PRPS 60 pivot point C is 25 mm; the shin carrier 20 is dimensioned such that the distance between KCPS 50 pivot point A and CBPS 70 pivot point B is around 179 mm; and the piston rod assembly 40 and the cylinder assembly 30 are dimensioned such that the distance between PRPS 60 pivot point C and CBPS 70 pivot point B is around 188 mm when the knee prosthesis 1 is fully extended and is 153 mm when the knee prosthesis 1 is fully flexed (i.e., the piston has a stroke of 35 mm). Additionally, pivot point B is offset from the axis of the piston and cylinder assembly (comprising the cylinder assembly 30 and the piston rod assembly 40) by 13.5 mm.

Anthropometic data of knee heights is provided in Table 1. The source of this data is "Anthropometry for Design for the Elderly", Kamal Kothiyal and Samuel Tettey, School of Safety Science, University of New South Wales, Sydney, Australia, published in International Journal of Occupational Safety and Ergonomics 2001, Vol. 7, No. 1, pages 15-34, which can be found here: http://dx.doi.org/10.1080/10803548.2001.11076474. The measurements are based on anthropometric data of elderly people in Sydney, Australia, which is the same age profile as the intended users of the present invention.

TABLE 1

Anthropometic data of knee heights

| | | | Percentile | | |
|---|---|---|---|---|---|
| | | Mean | 5 | 50 | 95 |
| Knee | Men | 515 | 470 | 513 | 570 |
| height | Women | 475 | 432 | 474 | 521 |
| (mm) | Average | 495 | 451 | 494 | 546 |

Since pivot point A corresponds to the knee pivot of an amputee and in use the pivot point A is typically between the 5th percentile of 432 mm (for women) and the 95th percentile of 570 mm (for men) above the base of the amputee's prosthetic foot, depending on the height of the amputee, then the distance of 179 mm between KCPS 50 pivot point A and CBPS 70 pivot point B is typically within the range of 31.4-41.4% of the height of pivot point A above the ground. In other words, the distance between pivot points A and B may be at least 25%, 30%, 35%, 40% or 45% of the height of the pivot point A above the base of such a foot prosthesis, depending on the height of the amputee.

The knee prosthesis 1 further comprises a micro-processor, an accumulator 92, a first valve, a second valve, a first motor and a second motor. The components of the knee prosthesis are configured and attached to each other in the manner described below.

The knee chassis 10 comprises a chassis body 12, a proximally directed pyramid connector 14, and a bolt 19 (best seen in FIG. 7) attaching the pyramid connector 14 to the chassis body 12. The chassis body 12 has a proximal portion and two substantially triangular posteriorly extending arms (partially shown in FIGS. 4 to 7). The two substantially triangular arms of the chassis body 12 each comprise a KCPS aperture 16 and a PRPS aperture 18. The KCPS apertures 16 on the two arms of the chassis body 12 are coaxially aligned and the PRPS apertures 18 on the two arms are coaxially aligned. The chassis body 12 is a single unitary piece of aluminium alloy. The proximally directed pyramid connector 14 is configured to align with an alignment coupling and a residuum socket (not shown).

The shin carrier 20 defines a hollow substantially semi-cylindrical cavity. The shin carrier 20 is a single unitary piece of aluminium alloy. The shin carrier 20 has a proximal end 22 and a distal end 24, and includes two coaxially aligned KCPS apertures 26 and two coaxially aligned CBPS apertures 28 (one KCPS aperture 26 and one CBPS aperture 28 being shown in FIG. 6). The two KCPS apertures 26 are located towards the proximal end 22 of the shin carrier 20. The two CBPS apertures 28 are located towards the distal end 24 of the shin carrier 20.

Figure 7:
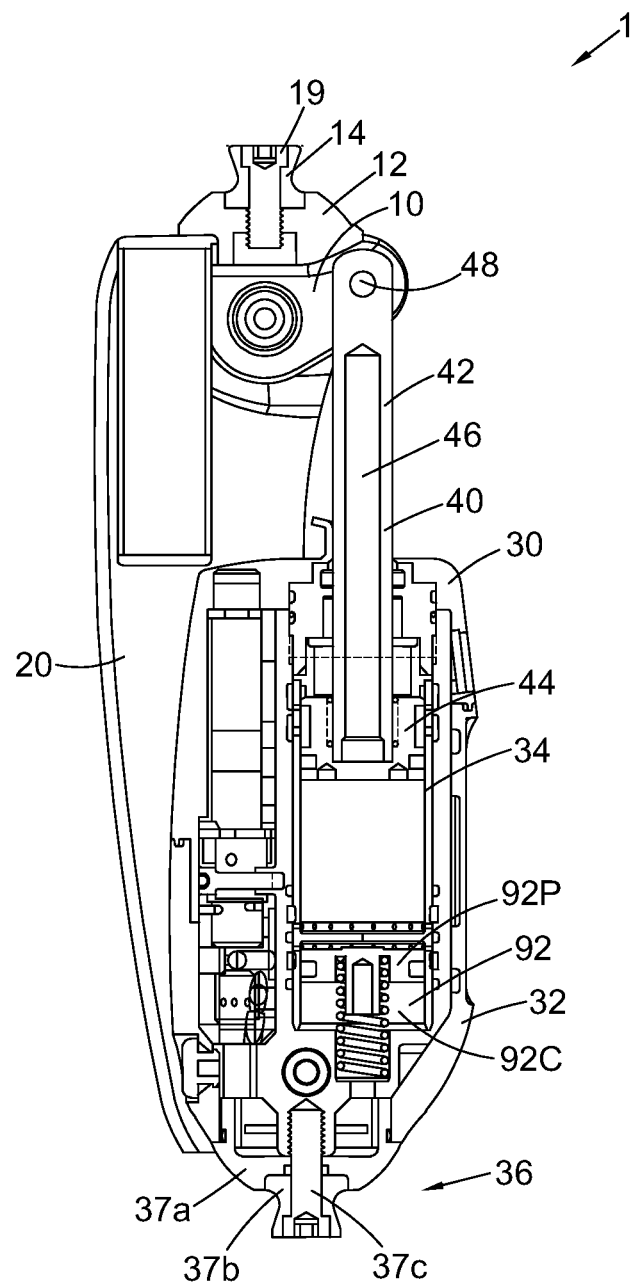
FIG. 7 is a cross-section through the embodiment shown in FIG. 4 on a sagittal plane passing through the middle of the prosthesis.

The cylinder assembly 30 comprises a cylinder body 32a, a cylinder body 32b, a cylinder sleeve 34 (best seen in FIG. 7) and a distally directed connector 36. The cylinder body 32a is substantially cylindrical and defines an interior cavity, a piston rod aperture 33 in its proximal end, a distally directed connector aperture 35 and a CBPS aperture 38a. The cylinder body 32b includes a CBPS aperture 38b and is made of aluminium alloy. The cylinder sleeve 34 defines an internal cylinder bore and is made of aluminium alloy. The cylinder sleeve 34 is configured to contain a fluid in the internal cylinder bore, such as a fluid suitable for use in a hydraulic circuit. The distally directed connector 36 comprises a main body 37a, a distally directed pyramid connector 37b and an attachment means 37c. The distally directed pyramid connector 37b is configured for connection to shin and ankle/foot components (not shown). For example, the distally directed pyramid connector 37b may be attached to a hydraulic ankle joint or to a hydraulic ankle/foot assembly as described in our patent application published as US-A1-2008/0262635. The attachment means 37c of the distally directed connector 36 is a bolt which is configured to attach the distally directed pyramid connector 37b to the main body 37a of the distally directed connector 36. Further, as can be seen in FIG. 7, the bolt 37c is screwed in to a distal portion of the cylinder sleeve 34 such that the pyramid connector 36 is rigidly attached to the internal cylinder bore of the cylinder sleeve 34. The outer housing 32a is attached to the cylinder body 32b. The cylinder body 32b is inserted into the cylinder sleeve 34. The cylinder body 32b is fixedly attached to the cylinder sleeve 34. The cylinder body 32b is also fixedly attached to the distally directed connector 36, the distally directed connector 36 being received in the distally directed connector aperture 35 of the outer housing 32a.

The piston rod assembly 40 comprises a piston rod 42 and a piston 44. The piston rod 42 is substantially cylindrical. The piston rod 42 is hollow and defines an inner cavity 46 and a PRPS aperture 48 at its proximal end. The inner cavity defined in the piston rod 42 is substantially cylindrical. The piston rod 42 is fixedly attached to the piston 44, by an attachment means such as a threaded connection. The piston rod 42 is a single unitary piece of titanium alloy, specifically Ti-6Al-4V. The piston rod 42 has an outer diameter of 14 mm and its cavity 46 has a diameter of 8 mm.

The knee chassis pivot shaft (KCPS) 50 comprises a first part and second part, the first and second parts each having a cylindrical body and a flange at one end of the cylindrical body. The first and second parts of the KCPS 50 are attachable to each other such that when attached, the flanges of the first and second parts are at outer ends of the KCPS 50. The KCPS 50 is configured so that at least one cylindrical body of the first or second part can be received in the KCPS apertures 26 of the shin carrier 20 and the KCPS apertures 16 of the knee chassis 10. The KCPS 50 is configured such that upon attachment to the knee chassis 10 and the shin carrier 20, the KCPS 50 cannot be removed from the knee chassis 10 or the shin carrier 20 without removal of the first part and the second part from each other. The KCPS 50 is configured such that upon attachment to the knee chassis 10 and the shin carrier 20, the knee chassis 10 and the shin carrier 20 are rotatable about a medial lateral central axis of the KCPS 50.

The piston rod pivot shaft (PRPS) 60 comprises a first part and second part, the first and second parts each having a cylindrical body and a flange at one end of the cylindrical body. The first and second parts of the PRPS 60 are attachable to each other such that when attached, the flanges of the first and second parts are at outer ends of the PRPS 60. The PRPS 60 is configured so that at least one cylindrical body of the first or second part can be received in the PRPS apertures 28 of the knee chassis 10 and the PRPS aperture 48 of the piston rod 42. The PRPS 60 is configured such that upon attachment to the knee chassis 10 and the piston rod 42, the PRPS 60 cannot be removed from the knee chassis 10 or the piston rod 42 without removal of the first part and the second part from each other. The PRPS 60 is configured such that upon attachment to the knee chassis 10 and the piston rod 42, the knee chassis 10 and the piston rod 42 are rotatable about a central axis of the PRPS 60.

The cylinder body pivot shaft (CBPS) 70 is similar to the KCPS 50 in that it comprises a first part and second part, the first and second parts each having a cylindrical body and a flange at one end of the cylindrical body. The first and second parts of the CBPS 70 are attachable to each other such that when attached, the flanges of the first and second parts are at outer ends of the CBPS 70. The CBPS 70 is configured so that at least one cylindrical body of the first or second part can be received in the CBPS apertures 28 of the shin carrier 20 and the CBPS aperture of the cylinder assembly 30. The CBPS 70 is configured such that upon attachment to the shin carrier 20 and the cylinder assembly 30, the CBPS 70 cannot be removed from the shin carrier 20 or the cylinder assembly 30 without removal of the first part and the second part from each other. The CBPS 70 is configured such that upon attachment to the shin carrier 20 and the cylinder assembly 30, the shin carrier 20 and the cylinder assembly assembly 30 are rotatable about a central axis of the CBPS 70.

The accumulator 92 comprises a spring-loaded piston 92P and a cylinder 92C which is an integral part of the cylinder sleeve 34 and is configured to store fluid. The accumulator 92 is configured to receive excess fluid displaced by the piston 44 when the piston 44 moves downwards. The accumulator 92 is configured to allow fluid to be supplied back to the cylinder assembly 30 when the piston 44 moves upwards.

The knee chassis 10, shin carrier 20, cylinder assembly 30, piston rod assembly 40, knee chassis pivot shaft (KCPS) 50, piston rod pivot shaft (PRPS) 60, and cylinder body pivot shaft (CBPS) 70 are attachable to each other in the following way.

The knee chassis 10 is connected to the shin carrier 20 by insertion of the KCPS 50 into the KCPS apertures 26 of the shin carrier 20 and the KCPS apertures 16 of the knee chassis 10. Upon attachment by the KCPS 50, the knee chassis 10 and shin carrier 20 are attached to each other, but free to rotate relative to each other about a medial lateral axis of the KCPS 50.

The shin carrier 20 is connected to the cylinder assembly 30 by insertion of the CBPS 70 into the CBPS apertures 28 of the shin carrier 20, and the CBPS apertures 38a, 38b of the outer housing 32a and cylinder body 32b. Upon attachment by the CBPS 70, the shin carrier 20 and cylinder assembly 30 are attached to each other, but free to rotate relative to each other about a medial lateral axis of the CBPS 70.

The piston rod assembly is translationally connected to the cylinder assembly 30. The piston 44 is received in the cylinder sleeve 34 of the cylinder assembly 30.

The piston rod assembly 40 is connected to the knee chassis 10 by insertion of the PRPS 60 into the PRPS apertures 18 of the knee chassis 10 and the PRPS aperture 48 of the piston rod 42. Upon attachment by the PRPS 60, the piston rod assembly 40 and the knee chassis 10 are attached to each other, but free to rotate relative to each other about a medial lateral axis of the PRPS 60.

Figure 8:
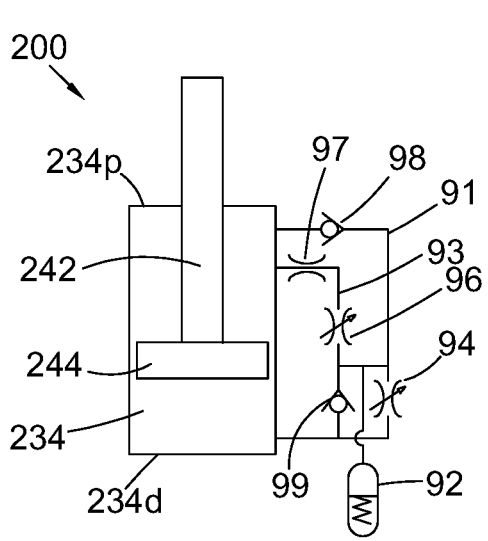
FIGS. 8 to 11 are schematics showing various alternatives for hydraulic circuits of the embodiment of the knee prosthesis.

FIG. 8 shows a hydraulic circuit 200 demonstrating how movement of the piston assembly, and consequently the knee prosthesis, is achieved. Hydraulic circuit 200 shows a piston rod 242, piston 244, a cylinder 234 having a proximal end 234p and a distal end 234d, and various control elements including: a terminal impact damper 97; a motor-controlled flexion flow control valve 94, a motor-controlled extension flow control valve 96; one-way valves 98, 99; and a spring loaded accumulator 92. Various control elements are fluidly connected by means of a flexion line 91 and an extension line 93 as shown in FIG. 8. Opening motor-controlled extension flow control valve 96 allows fluid to flow through the motor-controlled extension flow control valve 96. This permits piston 244 to move in the cylinder 234 away from the distal end of the cylinder 234d towards the proximal end of the cylinder 234p, causing the knee prosthesis to move in a manner demonstrated by the progression of movement of the prosthesis shown by FIG. 14, then FIG. 13, then FIG. 12, corresponding to knee extension.

Opening motor-controlled flexion flow control valve 94 allows fluid to flow through the motor-controlled flexion flow control valve 94. This permits piston 244 to move in the cylinder 234 away from the proximal end of the cylinder 234p towards the distal end of the cylinder 234d, causing the knee prosthesis to move in a manner demonstrated by the progression of movement of the prosthesis shown by FIG. 12, then FIG. 13, then FIG. 14, corresponding to knee flexion.

Figure 12:
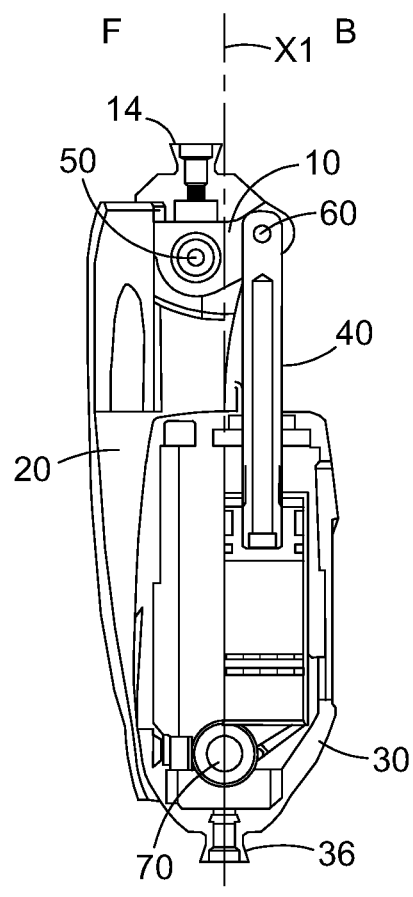
FIGS. 12, 13 and 14 are simplified cross-sections through the embodiment of FIG. 4 in a first position, a second position and a third position respectively.
Figure 13:
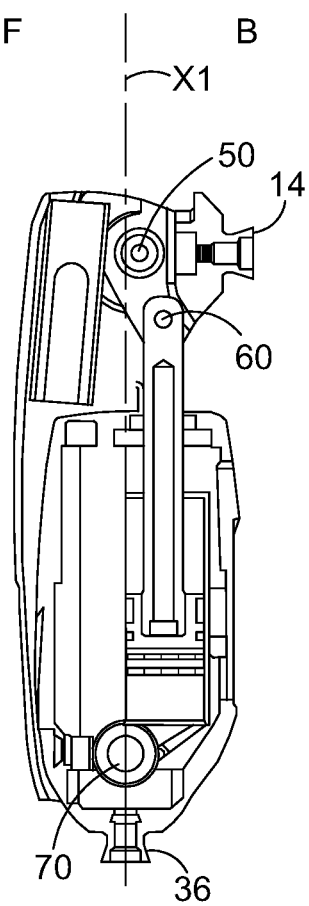
Figure 14:
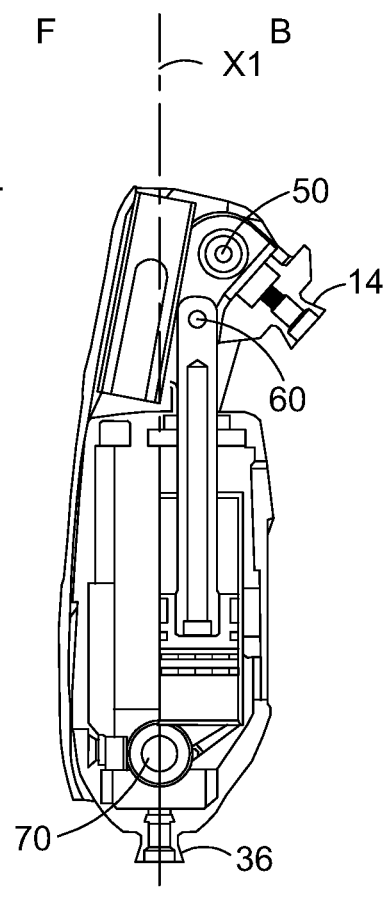

FIGS. 12 to 14 are shown as aligned with each other relative to an axis X1 of distally directed connector 36. It should be noted that in use the knee prosthesis rotates and translates relative to its attachment (by means of proximally directed pyramid connector 14) to a residuum socket (not shown). Hence, in general terms, relative movement of the knee chassis 10 and the distally directed connector 36 (which in FIGS. 12 to 14 is shown as rotation clockwise of the knee chassis 10 relative to the distally directed connector 36) in use would involve a knee chassis 10 fixed to a residuum socket, and rotation of the remainder of the knee prosthesis anticlockwise about the knee chassis 10.

Figure 9:
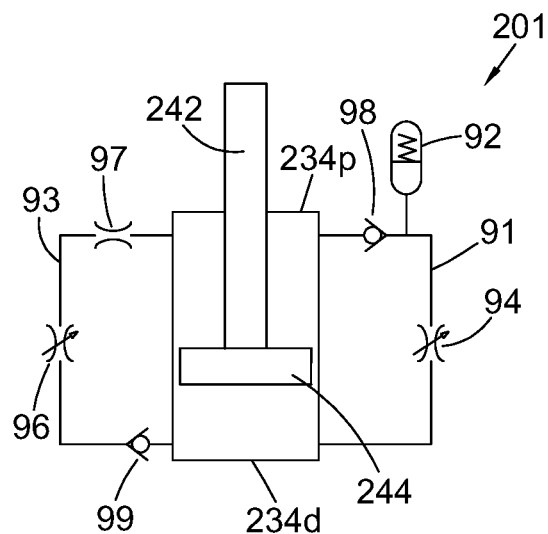

FIG. 9 shows an alternative hydraulic circuit 201. Similar to the hydraulic circuit shown in FIG. 8, hydraulic circuit 201 shows a piston rod 242, a piston 244, a cylinder 234 having a proximal end 234p and a distal end 234d, and various control elements including: a terminal impact damper 97; motor-controlled flexion flow control valve 94, motor-controlled extension flow control valve 96; one-way valves 98, 99; and a spring loaded accumulator 92. Various control elements are fluidly connected by means of a flexion line 91 and an extension line 93. The hydraulic circuit of FIG. 9 differs from the hydraulic circuit shown in FIG. 8 in that the accumulator 92 is connected to the flexion line 91 only, as opposed to being connected to both the flexion line 91 and the extension line 93 as in the hydraulic circuit 200 of FIG. 8. The hydraulic circuit shown in FIG. 9 has a micro-processor controlled (MPC) flexion flow control valve 94 and a manual extension flow control valve 96.

Figure 10:
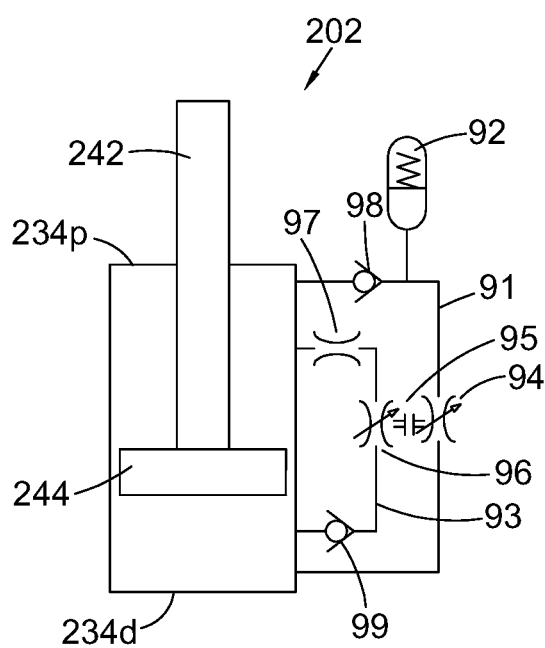

FIG. 10 shows an alternative hydraulic circuit 202. Similar to the hydraulic circuits shown in FIGS. 8 and 9, hydraulic circuit 202 shows a piston rod 242, a piston 244, a cylinder 234 having a proximal end 234*p* and a distal end 234*d*, and various control elements including: a terminal impact damper 97; motor-controlled flexion flow control valve 94, motor-controlled extension flow control valve 96; one-way valves 98, 99; and a spring loaded accumulator 92. Various control elements are fluidly connected by means of a flexion line 91 and an extension line 93 as shown in FIG. 10. The hydraulic circuit of FIG. 10 differs from the hydraulic circuit shown in FIG. 8 and FIG. 9 in that there is a single motor 95 which is used to control the motor-controlled flexion flow control valve 94 and the motor-controlled extension flow control valve 96. Optionally, the motor is controlled by micro-processor, moving both valves either simultaneously or in sequence.

Figure 11:
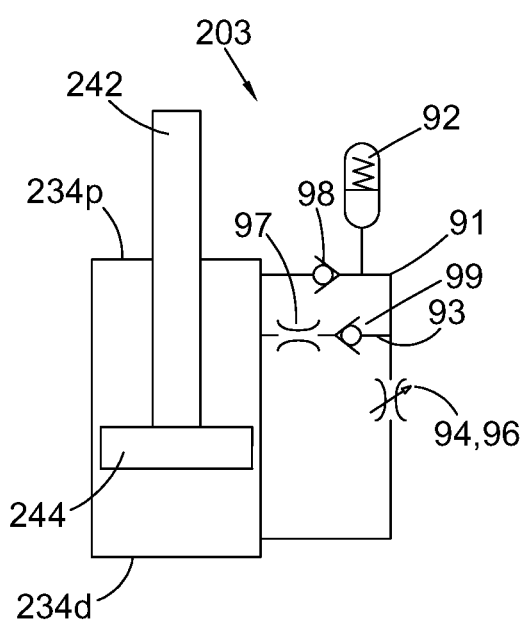

FIG. 11 shows an alternative hydraulic circuit 203. Similar to the hydraulic circuits shown in FIGS. 8, 9 and 10, hydraulic circuit 203 shows a piston rod 242, a piston 244, a cylinder 234 having a proximal end 234*p* and a distal end 234*d*, and various control elements including: a terminal impact damper 97; a valve 94, 96 which acts as a flow control valve for both flexion and extension; one-way valves 98, 99; and a spring loaded accumulator 92. Various control elements are fluidly connected by means of a line 91 for both flexion and extension flows as shown in FIG. 11. The hydraulic circuit of FIG. 11 differs from the hydraulic circuit shown in FIGS. 8 to 10 in that there is a single bi-directional valve which is both a motor-controlled extension flow control valve and a motor-controlled flexion valve. The hydraulic circuit 203 of FIG. 11 is advantageous compared to the hydraulic circuit 202 of FIG. 10 in that it is simpler, however is disadvantageous in that the motor controlling the valve must move further than the motor used to control the valve in FIG. 10. Optionally, the valve movement is micro-processor controlled.

FIGS. 12 to 14 each show an axis X1, which bisects distally directed connector 36 and CBPS 70. In the views shown in FIGS. 12 to 14, axis X1 defines a front side F and a back side B. Considering the movement shown in FIGS. 12 to 14 relative to a hypothetically stationary distally directed connector 36 (as illustrated) shows that there is not only rotation of the knee chassis 10 but also translation. In FIG. 12, KCPS 50 is on the front side F, and PRPS 60 is on the back side B of the axis X1. In FIG. 13, both KCPS 50 and PRPS 60 are on the back side B of the axis X1, with PRPS 60 being further away from the axis X1 than KCPS 50. In FIG. 14, both KCPS 50 and PRPS 60 are on the back side B of the axis X1, however KCPS 50 is further away from the axis X1 than PRPS 60. Movement of KCPS 50 in this way is a key feature of polycentric movement of the lower limb prosthesis, and is referred to herein as a posterior shift.

As the skilled person will appreciate in light of the above disclosure, the cylinder assembly 30 and piston rod assembly 40 are not free to rotate relative to distally directed connector 36, hence these components are subjected to not only axial stresses, but also a bending moment. In order to withstand the bending moments to which the piston rod 42 is subjected, its diameter is increased, for example, relative to the piston rod 18C' of FIG. 1. On the other hand, in order to not adversely affect the overall weight of the prosthesis, piston rod 42 is hollow, having a cavity 46. This has the advantage of providing a higher strength to weight ratio than a solid piston rod whilst having sufficient bending stiffness.

FIGS. 15 to 18 show cross-sections through a second embodiment of the present knee prosthesis 3. The second embodiment of the present knee prosthesis 3 is similar to the first embodiment 1 in that it is a polycentric linkage (as represented in FIG. 3), in which the cylinder body link is configured for attachment to a shank and/or a foot prosthesis.

For clarity, only the key differences between the first and second embodiments will be described. Reference numerals used to label the second embodiment shown in FIGS. 15 to 18 correspond to those of similar or identical components the first embodiment described in relation to FIGS. 4 to 14, but preceded by the number "3". For example, the knee chassis "10" of the first embodiment knee prosthesis 1 corresponds to the knee chassis "310" of the second embodiment knee prosthesis 3.

Figure 15:
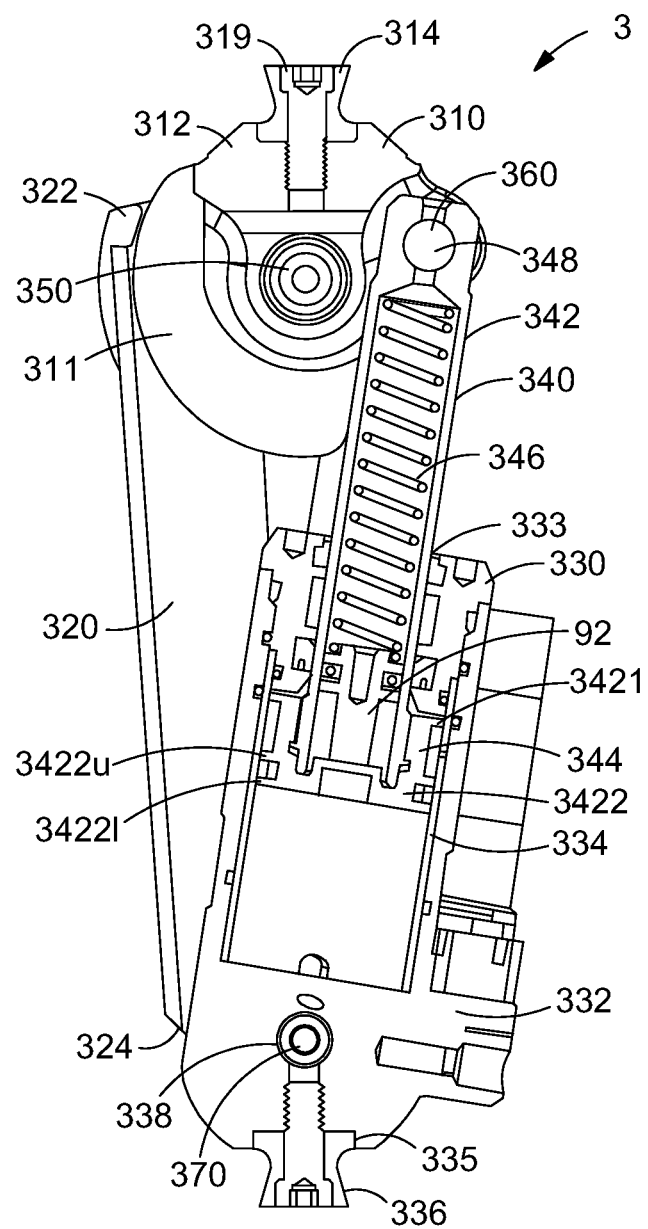
FIG. 15 is a cross-section through a second embodiment of a knee prosthesis in accordance with the invention, on a sagittal plane passing through the middle of the prosthesis.

As shown in FIG. 15, the knee prosthesis 3 comprises: a knee chassis 310, a shin carrier 320, a cylinder assembly 330, and a piston rod assembly 340, a knee chassis pivot shaft (KCPS) 350, a piston rod pivot shaft (PRPS) 360, and a cylinder body pivot shaft (CBPS) 370. The knee prosthesis 3 comprises a micro-processor. The knee chassis 310, the shin carrier 320, the cylinder assembly 330, and the piston rod assembly 340, correspond respectively to: the knee chassis link 110, the shin carrier link 120, the cylinder body link 130, and the piston rod assembly link 140 described above in relation to FIG. 3. The KCPS 50, CBPS 70 and PRPS 60 correspond to pivot points A, B and C of FIG. 3 respectively.

In the knee prosthesis 3 of FIGS. 15 to 18 the knee chassis 310 is dimensioned such that the distance between KCPS 350 pivot point A and PRPS 360 pivot point C is 25 mm; the shin carrier 320 is dimensioned such that the distance between KCPS 350 pivot point A and CBPS 370 pivot point B is around 146 mm; and the piston rod assembly 340 and the cylinder assembly 330 are dimensioned such that the distance between PRPS 360 pivot point C and CBPS 370 pivot point B is around 154 mm when the knee prosthesis 3 is fully extended and is 121 mm when the knee prosthesis 3 is fully flexed (i.e., the piston has a stroke of 33 mm). Referring again to Table 1, the distance between KCPS 350 pivot point A and CBPS 370 pivot point B is typically within the range of 25.6-33.8% of the height of pivot point A above the ground. In other words, the distance between pivot points A and B may be at least 20%, 25%, 30%, 35% or 40% of the height of the pivot point A above the base of such a foot prosthesis.

Second embodiment knee chassis 310 is similar to first embodiment knee chassis 10 in that it comprises a chassis body 312, a proximally directed pyramid connector 314, and an attachment means 319 in the form of a bolt.

Second embodiment shin carrier 320 is similar to first embodiment shin carrier 20 in that it defines a hollow substantially semi-cylindrical cavity. The shin carrier 320 is a single unitary piece of aluminium alloy. The shin carrier 320 is similar to the first embodiment shin carrier 20 in that it has a proximal end 322 a distal end 324, and defines two KCPS apertures and two CBPS apertures (not shown). The two KCPS apertures are located at the proximal end 322 of the shin carrier 320, and the two CBPS apertures are located at the distal end 324 of the shin carrier 320.

The second embodiment cylinder assembly 330 is similar to first embodiment cylinder assembly 30 in that it comprises a cylinder body 332, a cylinder sleeve 334, and a distally directed connector 336. The cylinder body 332 is cylindrical and defines an interior cavity, a piston rod aperture 333, a distally directed connector aperture 335 and a CBPS aperture 338. The cylinder sleeve 334 defines an internal cylindrical bore. The cylinder sleeve 334 is configured to contain a fluid in the internal cylindrical bore, such as a fluid suitable for use in a hydraulic circuit. The distally directed connector 336 comprises a distally directed pyramid connector and an attachment means. In contrast to the distally directed connector 36 of the first embodiment cylinder assembly 30, the distally directed connector 336 does not comprise a main body. Instead of having a main body, the pyramid connector and attachment means of the distally directed connector 336 are attached directly to the cylinder body 332 of the second embodiment cylinder assembly 330. Similar to the first embodiment cylinder assembly 30, the distally directed pyramid connector is configured for connection to shin and foot components (not shown). The cylinder sleeve 334 is fixedly attached to the cylinder body 332.

The second embodiment piston rod assembly 340 is similar to the first embodiment piston rod assembly 40 in that it comprises a piston rod 342 and a piston 344. The piston rod 342 is substantially cylindrical. The piston rod 342 defines an inner cavity 346 and a PRPS aperture 348. The inner cavity defined in the piston rod 342 is substantially cylindrical. The piston 342 has a proximal end and a distal end. The piston 342 has a proximal cylindrical flange 3421 and a distal cylindrical flange 3422, the proximal cylindrical flange 3421 being located at the proximal end of the piston 342, and the distal cylindrical flange 3422 being located at the distal end of the piston 342 as shown in FIG. 15. The distal cylindrical flange 3422 has an upper cylindrical flange part 3422*u*, and a lower cylindrical flange part 34221, between which a groove is defined. The groove is configured to receive a seal. The piston 344 is fixedly attached to the piston rod 342, by an attachment means such as a threaded connection. The piston rod 42 is a single unitary piece of titanium alloy, specifically Ti-6Al-4V. In contrast to the first embodiment piston rod 42, the second embodiment piston rod 342 has an outer diameter of 20 mm and an inner diameter of 16 mm. In contrast to the arrangement of the first embodiment, an accumulator (the piston 92 of which is shown in FIG. 15) is present in the inner cavity 346 of the piston rod 342 of the second embodiment. This feature will be further described in relation to FIG. 19.

Figures 16, 17, 18:
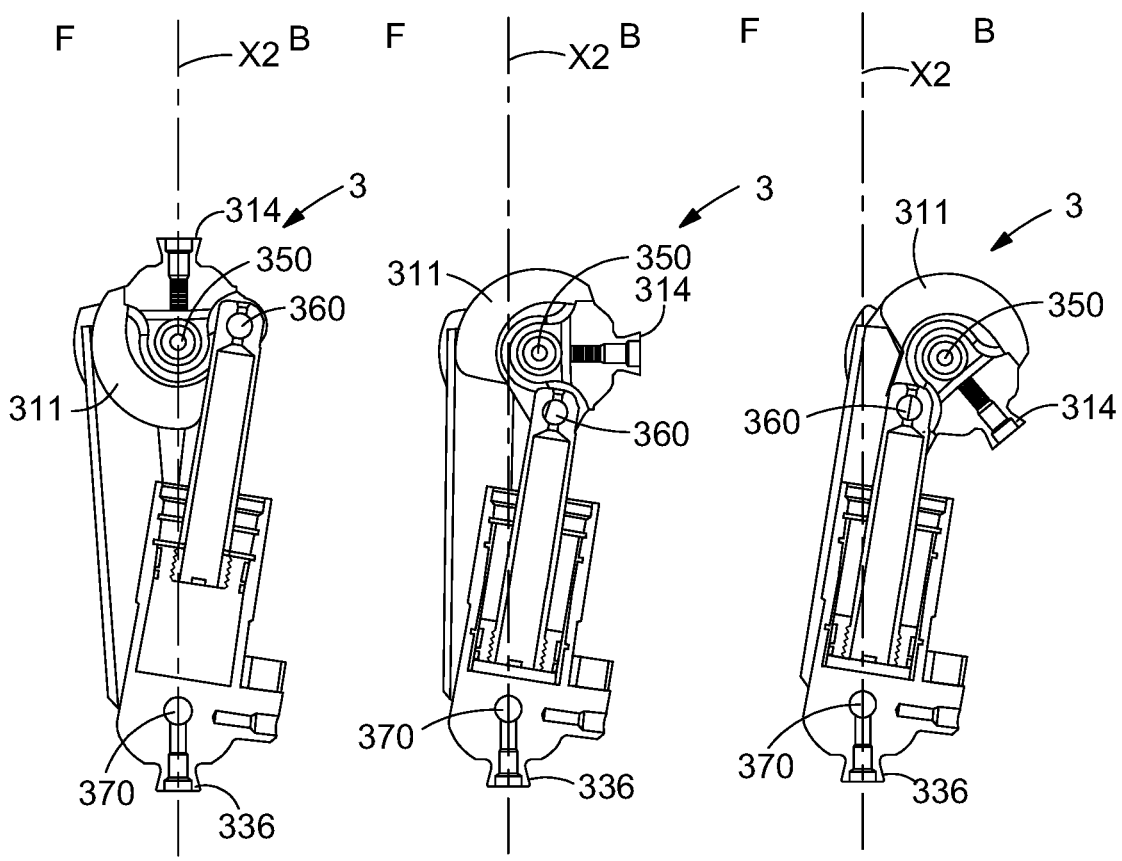
FIGS. 16, 17 and 18 are simplified cross-sections through the embodiment of FIG. 15 in a first position, a second position and a third position respectively.

The second embodiment knee chassis pivot shaft (KCPS) 350, the piston rod pivot shaft (PRPS) 360 and the cylinder body pivot shaft (CBPS) 370 are the similar to the first embodiment knee chassis pivot shaft (KCPS) 50, the piston rod pivot shaft (PRPS) 60 and the cylinder body pivot shaft (CBPS) 70, in that they are configured to provide pivot connections between the knee chassis 310, the shin carrier 320, the cylinder assembly 330 and the piston rod assembly 340 as described above in relation to the first embodiment, and configured so that the second embodiment can move in the same way as the first embodiment, as will be described in relation to FIGS. 16 to 18.

FIGS. 16 to 18 each show an axis X2, which bisects distally directed connector 336 and CBPS 370. In the views shown in FIGS. 16 to 18, axis X2 defines a front side F and a back side B. The second embodiment knee prosthesis 3 is configured to move in a similar manner to first embodiment knee prosthesis 1. As with the first embodiment, movement of the knee chassis 310 relative to a hypothetically stationary distally directed connector 336 involves both rotation and translation of the knee chassis 310. In FIG. 16, KCPS 350 is on the front side F, and PRPS 360 is on the back side B of the axis X2. In FIG. 17, both KCPS 350 and PRPS 360 are on the back side B of the axis X2, with PRPS 360 being further away from the axis X2 than KCPS 350. In FIG. 18, both KCPS 350 and PRPS 360 are on the back side B of the axis X2, however KCPS 350 is further away from the axis X2 than PRPS 360. Movement of KCPS 350 in this way is a key feature of polycentric movement of the lower limb prosthesis, and is referred to herein as a posterior shift.

Figure 19:
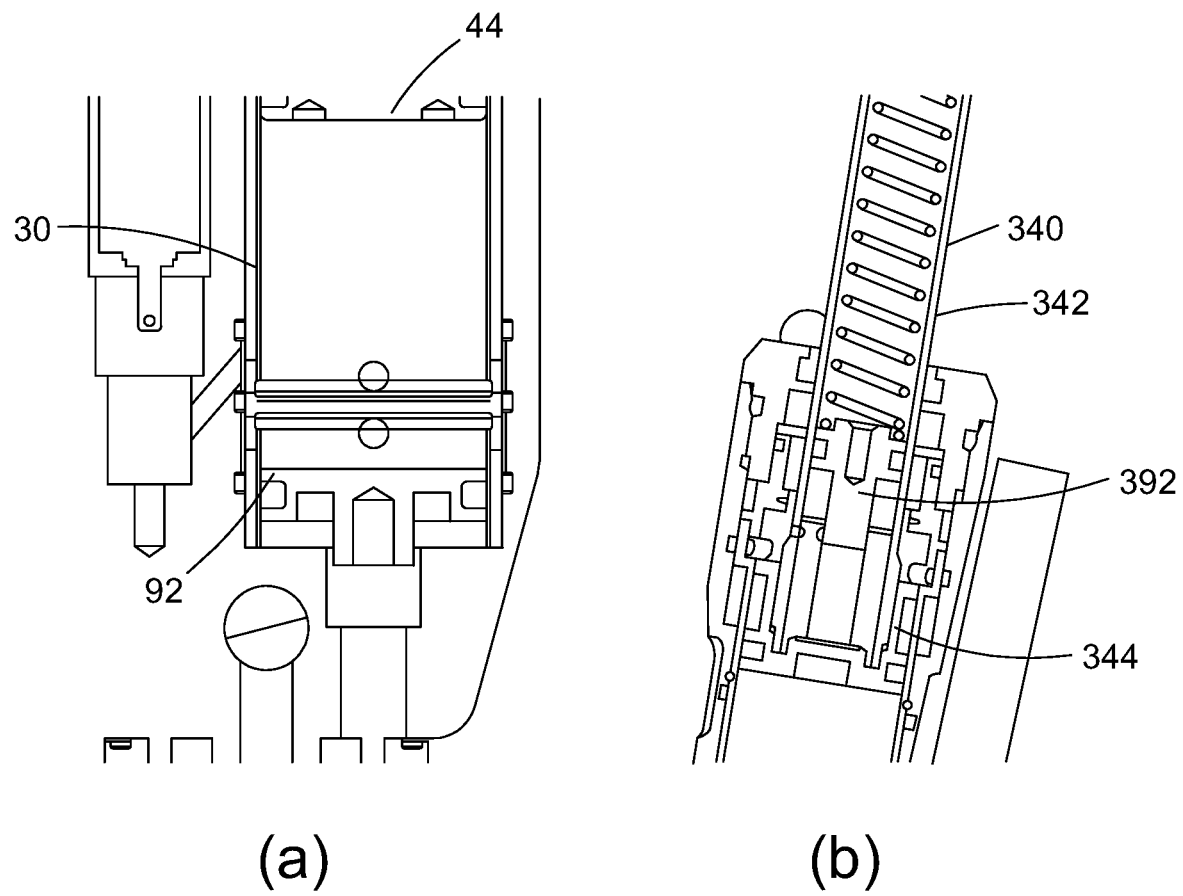
FIGS. 19A and 19B are enlarged cross-sections of parts of (a) the first embodiment; and (b) the second embodiment.

FIG. 19 is an enlarged cross-section of (a) the first embodiment; and (b) the second embodiment showing the arrangement of the accumulator in the knee prosthesis. Differences between the first and second embodiment lower limb prostheses will be elaborated in relation to the location and configuration of the accumulator.

As shown in FIG. 19 (*a*), in the first embodiment, the accumulator 92 is located proximate, specifically below, the cylinder assembly 30.

As shown in FIG. 19 (*b*), in the second embodiment, the accumulator 92 is located inside the piston rod assembly 340, specifically the accumulator 92 is located inside the inner cavity 346 of the piston rod 342.

The first embodiment knee prosthesis 1 has several advantages over the second embodiment knee prosthesis 3, which include (but are not limited to): having a smaller diameter piston rod 42 (14 mm compared to 20 mm for the second embodiment), providing more available space in the arrangement for a battery pack than the second embodiment; being less complex; having a lower quality requirement, and lower associated cost, for the piston rod 342; less accumulator piston displacement (approximately 7 mm compared to approximately 50 mm for the second embodiment) and less subsequent risk of noise due to friction.

However, the first embodiment knee prosthesis 1 also has several disadvantages over the second embodiment knee prosthesis 3, which include (but are not limited to): a more complex cylinder sleeve; and a longer arrangement.

Equally, the second embodiment knee prosthesis 3 has several advantages over the first embodiment knee prosthesis 1, which include (but are not limited to): utilising otherwise unused space in the piston rod 342; and being shorter than the first embodiment knee prosthesis 1.

The second embodiment knee prosthesis 3 also has several disadvantages over the first embodiment knee prosthesis 1, which include (but are not limited to): requirement for a controlled surface finish on the internal surface of the piston rod 342, and associated cost; large accumulator spring displacement and associated spring fatigue limiting spring lifetime; and a larger displacement of the accumulator piston and higher risk of noise due to friction.

As a skilled person will appreciate, the human knee joint is an open joint in which the articular surfaces bear compressive loads, but do not substantially constrain the relative movement between the bones. This is in contrast with closed anatomic joints, in which the geometry of the articular surfaces define a centre of rotation (e.g. in the elbow or the hip joints). The combined action of the ligaments around the knee joint constrain the movement of the joint and makes it polycentric. Considering only the sagittal plane, the cruciate ligaments together with the femur and tibia form a four bar linkage. As a skilled person will appreciate, as the human knee joint moves, the instantaneous centre of rotation (ICR) changes, and the joint is polycentric. In particular, the polycentric movement is achieved by the combination of articular cartilage working in compression, collateral ligaments working in tension, and the cruciate ligaments. The knee pivot axis in a human knee undergoes a posterior shift during knee flexion.

Although the posterior shift in the first and second embodiment knee prostheses is achieved by a mechanically different mechanism to the posterior shift in a human knee, the presence of a posterior shift in the first and second embodiments can be seen to mimic movement in a human knee. This has various aesthetic advantages, as well as a potentially improved user experience by the user of the first or second embodiment knee prosthesis.

As the skilled person will appreciate in light of the above disclosure, in the second embodiment (in the same manner as the first embodiment) the cylinder assembly 330 and piston rod assembly 340 are not free to rotate relative to distally directed connector 336, hence these components are subjected to not only axial stresses, but also a bending moment. As shown in FIGS. 15 to 18, piston rod 342 has a cavity 346. As with the first embodiment, this has the advantage of providing a higher strength to weight ratio than a solid piston rod, and also a higher bending stiffness to weight ratio.

In the embodiments described above the connector 36, 336 that is configured to connect to shin and foot components, and the connector 14, 314 that is configured to align with an alignment coupling and a residuum socket, are pyramid connectors. In other embodiments, these connectors are any appropriate shape.

In the embodiments described above, various features are described as fixedly attached to each other. For example, the pyramid connectors are described as fixedly attached to other components by means of a threaded attachment (for example a threaded screw and hole). It should be understood that any other appropriate attachments means is possible. It should also be understood that various components could be integrally formed with one another as a single unitary piece.

In the embodiments described above, the piston rod is described as defining a substantially cylindrical internal cavity. It will be understood by the skilled person that although a cylindrical cavity has various advantages in terms of giving the component a high strength to weight ratio, any appropriate shape of internal cavity could be used.

Although specific details of the pivot connections (KCPS, CBPS, PRPS) have been given, it should be understood that various connections which allow the attached components to pivot relative to each other may be suitable.

Although the accumulator described as used in the knee prosthesis is a spring loaded accumulator, it will be appreciated that any suitable accumulator could be used, for example a gas charged accumulator.

Although specific materials have been provided for components such as the chassis body, the cylinder body, the shin carrier, such as aluminium alloy, it should be understood that any suitable material can be used. Preferably, these components comprise mechanical and material properties equal to or similar to aluminium alloy.

Although specific inner and outer diameters have been provided for the piston rod, it should be understood that such diameters may differ from those provided. The specific diameters provided are optimal for the embodiment described. However, as will be understood by a person skilled in the art, diameters similar to those provided are equally applicable.

Although a specific form and arrangement of knee prosthesis is shown in the Figures, it will be appreciated that various aesthetic changes could be made to the device shown whilst still performing the function of the present invention as defined in the appended claims.

Figure 1B:
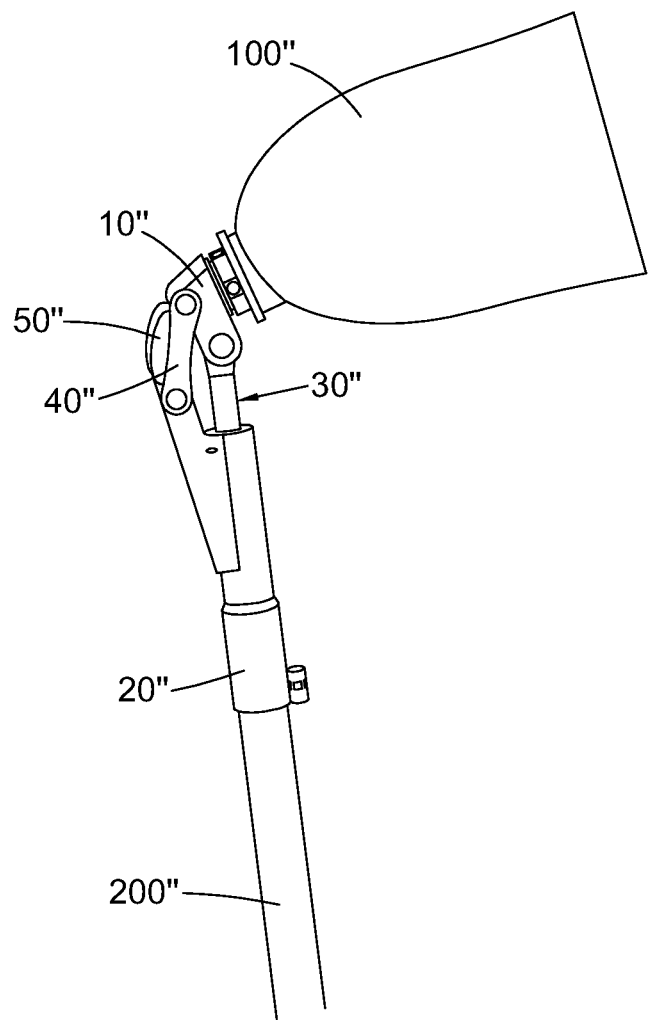
FIG. 1B is side elevation of a second prior art lower limb prosthesis.
Figure 20A:
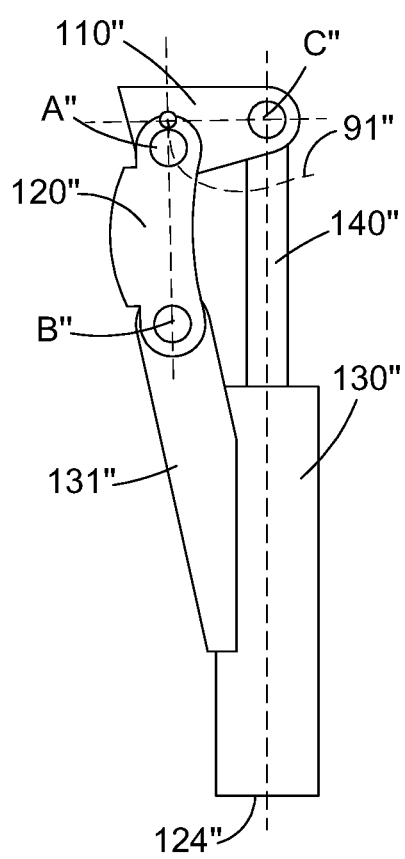
FIG. 20A is a schematic representation of the prior art prosthesis of FIG. 1B, showing the instantaneous centre of rotation path (centrode) through rotation of the prosthesis.
Figure 20B:
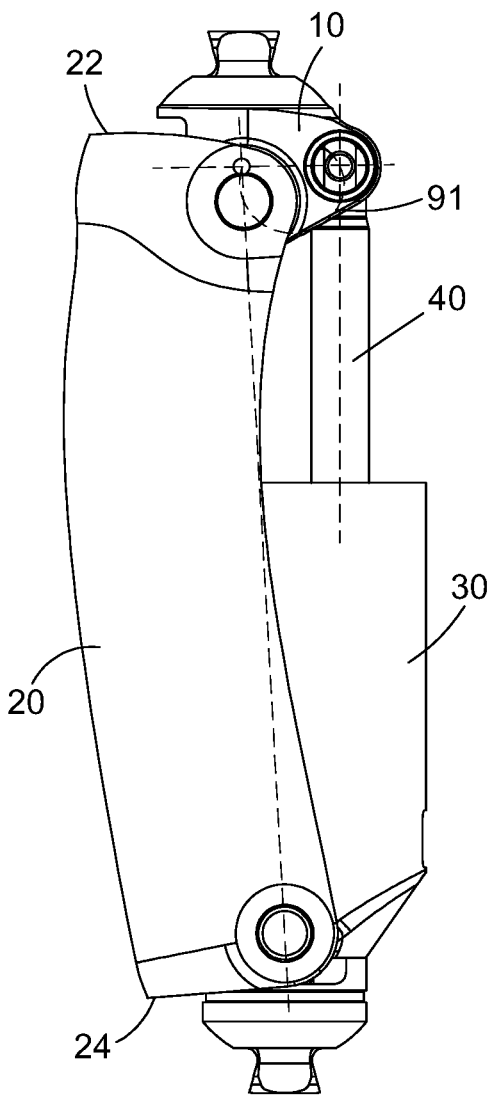
FIG. 20B is a schematic representation of the first and second embodiment prostheses of the knee prosthesis in accordance with the invention, showing the centrode through rotation of the prosthesis.

A schematic of the prior art device of FIG. 1B is shown in FIG. 20A, and a schematic of the first embodiment of the present invention is shown in FIG. 20B.

Figure 21A:
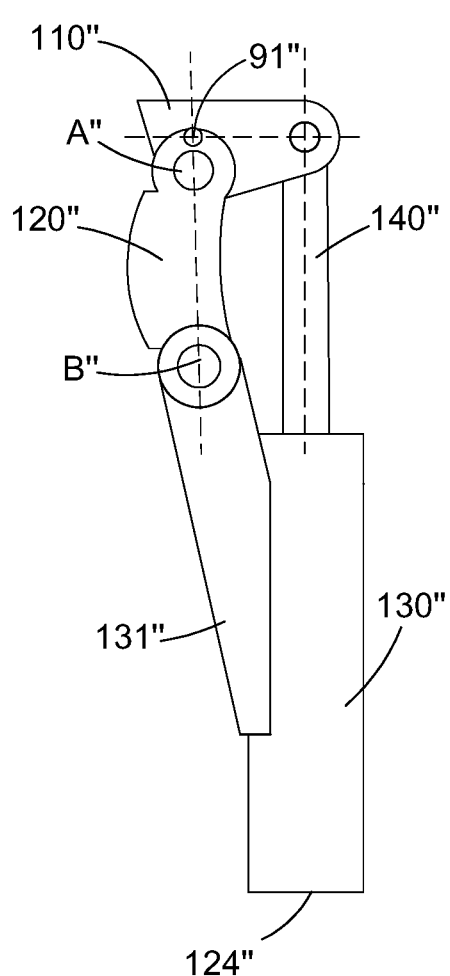
Figure 22A:
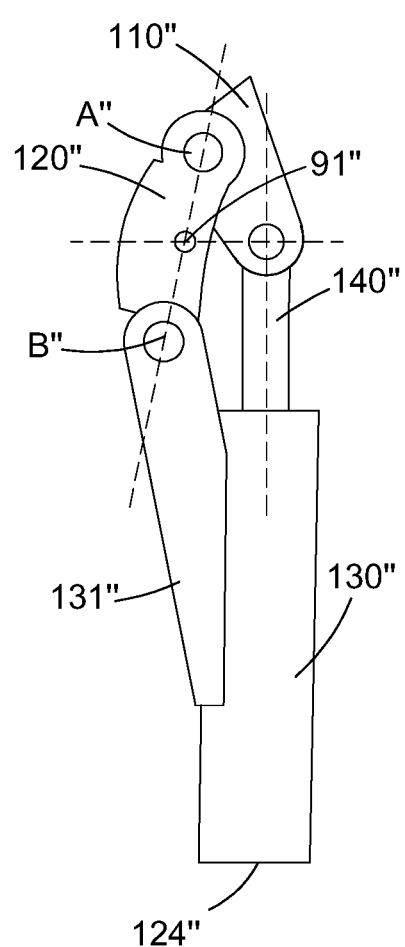
Figure 23A:
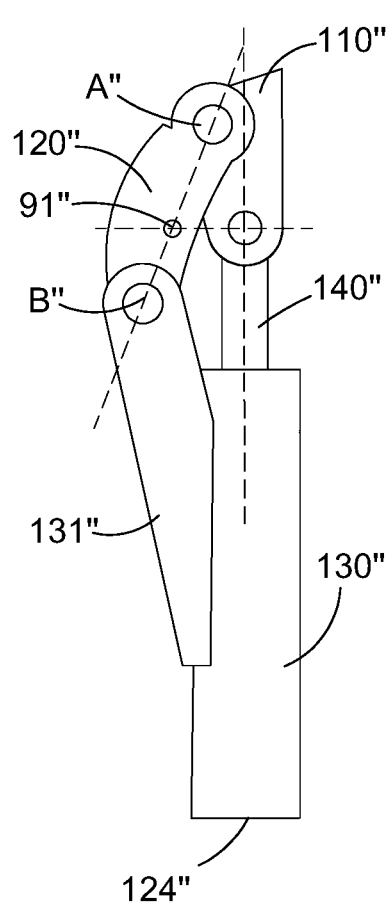
Figure 23B:
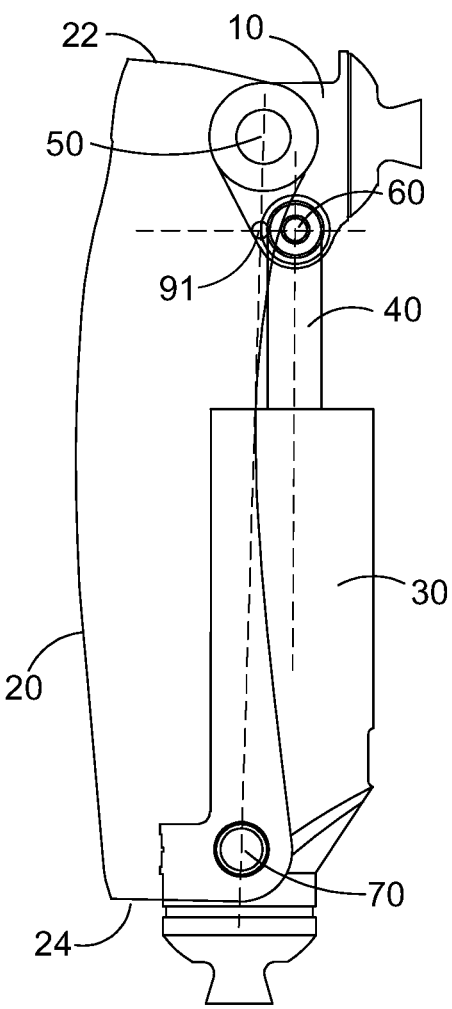

FIGS. 21A, 22A and 23A are annotated schematics showing how the instantaneous centre of rotation 91" is determined at three different positions of the prior art prosthesis schematic.

Figure 21B:
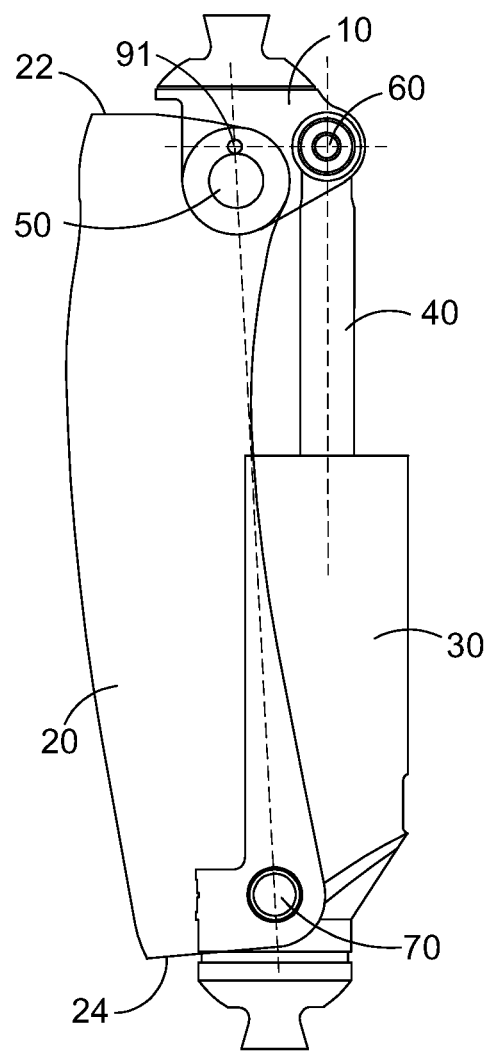
Figure 22B:
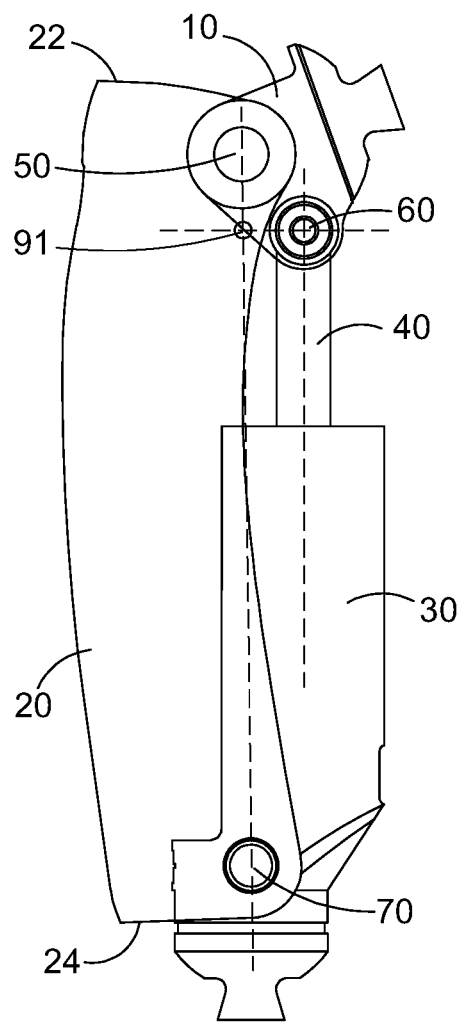

FIGS. 21B, 22B, and 22B are annotated schematics showing how the centrode 91 is determined at three different positions of the prior art prosthesis schematic.

FIG. 20A shows a centrode 91" of the prior art prosthesis (as determined by the present inventor), and FIG. 20B shows the centrode 91 of the first embodiment of the present invention.

As shown in FIG. 20B, the centrode 91 of the first embodiment substantially defines a semi-circle circumference, specifically ⅔ of a circle circumference. In the first embodiment of the present invention, the centrode 91 intersects the knee chassis at the start and the end of the movement shown. In the first embodiment of the present invention, the cylinder assembly 30 is pivotally connected to the shin carrier 20 proximate to the foot component or the connection to a foot component 36. In the first embodiment of the present invention, the shin carrier 20 has a longitudinal dimension, defined between the proximal end 22 and the distal end 24, the longitudinal dimension being longer than the stroke length of the piston assembly.

The second embodiment prosthesis of the present invention has a similar centrode to the first embodiment prosthesis of the present invention.

In contrast, as shown in FIG. 20A, the centrode 91" of the prior art schematic defines a shape having an arcuate portion and a substantially linear portion. Specifically, the arcuate portion substantially defines a quarter of a circle circumference. In the prior art schematic of FIG. 20A, the centrode 91" does not intersect the knee chassis at the start and the end of the gait cycle. In the prior art schematic of FIG. 20A, the cylinder body 130" is pivotally connected to the shin carrier 120" at a point distal to the foot component or the connection to a foot component. Specifically, the cylinder body 130" is pivotally connected to the shin carrier 120" at an end of an arm 131" of the cylinder body 130". The end of the arm 131" is a furthest point of the cylinder body 130" from a foot component or connection to a foot component. In the prior art schematic of FIG. 20A, the shin carrier 120" has a functional longitudinal dimension, defined between pivot points A" and B", this longitudinal being shorter than the stroke length of the piston assembly.

The first 1 and second 3 embodiment knee prostheses of the present invention have various advantages compared to the knee prosthesis of (illustrated in FIG. 1B and interpreted by the herein in FIGS. 20A, 21A, 22A and 23A).

These advantages include, but are not limited to the advantages given in the following list:

a) In prior art prostheses, when an amputee stands up from a sitting position with the prosthesis on, standing up pulls the socket away from the stump, and requires the amputee to push the stump back into the socket once vertical. The present invention addresses this deficiency and allows the amputee to rise more naturally from a sitting position. This advantage is made possible by the narrow (i.e. short in a horizontal direction) ICR path, as demonstrated with the present invention.

b) The toe clearance during the swing phase with the present invention is better than with the prosthesis of FIG. 1B.

c) The present invention has a mechanical advantage, due to the comparative greater length of the anterior shin carrier.

A microprocessor system may be used with the present invention to compensate for a less stable prosthesis as compared to the prior art prosthesis shown in FIG. 1B and interpreted herein with the schematics in FIGS. 20A, 21A, 22A and 23A.

The invention claimed is:

1. A lower limb prosthesis, comprising:
   a knee chassis;
   a shin carrier pivotally connected to the knee chassis; and
   a piston and cylinder assembly pivotally connected to the knee chassis and the shin carrier, the piston and cylinder assembly comprising:
      a piston assembly comprising a piston mounted on a piston rod; and
      a cylinder body having a cavity defining a cylinder within which the piston is arranged to reciprocate;
   wherein:
      the knee chassis is pivotally connected to the shin carrier to pivot around an anterior knee pivot axis (A);
      the knee chassis is pivotally connected to the piston and cylinder assembly to pivot around a posterior knee pivot axis (C); and
      the shin carrier is pivotally connected to the piston and cylinder assembly to pivot around a distal pivot axis (B),
   wherein the piston and cylinder assembly further comprises, distal to the distal pivot axis (B), a foot component having a distal surface, and a distance from the anterior knee pivot axis (A) to the distal pivot axis (B) is more than 20% of a distance from the anterior knee pivot axis (A) to the distal surface of the foot component, or
   the piston and cylinder assembly further comprises, distal to the distal pivot axis (B), a connector for attaching a foot component to the piston and cylinder assembly, said foot component having a distal surface, and, in use, when said foot component is attached to the connector a distance from the anterior knee pivot axis (A) to the distal pivot axis (B) is more than 20% of a distance from the anterior knee pivot axis (A) to the distal surface of said foot component,
   wherein the piston and cylinder assembly, the knee chassis and the shin carrier define a polycentric linkage.

2. The lower limb prosthesis as claimed in claim 1, wherein the distance between the anterior knee pivot axis (A) and the distal pivot axis (B) is more than 20%, 25%, 30%, 35%, 40% or 45% of the distance from the anterior knee pivot axis (A) to the distal surface of the foot component.

3. The lower limb prosthesis as claimed in claim 1 and further comprising a controller configured to control relative movement between the cylinder body and the piston assembly.

4. The lower limb prosthesis as claimed in claim 3, wherein the controller is configured to control relative movement between the cylinder body and the piston assembly in dependence on the position of the prosthesis in a gait cycle.

5. The lower limb prosthesis as claimed in claim 3, wherein the controller is a hydraulic or pneumatic controller, comprising at least one electronically-controlled valve.

6. The lower limb prosthesis as claimed in claim 3, wherein the controller comprises a micro-processor, the micro-processor being comprised in or on the lower limb prosthesis.

7. The lower limb prosthesis as claimed in claim 1, wherein the cylinder body comprises a cylinder sleeve, the cylinder sleeve being configured to receive the piston such that translational movement of the piston within the cylinder sleeve is permitted, and the connector is fixedly attached to or forms part of the cylinder sleeve.

8. The lower limb prosthesis as claimed in claim 1, wherein the foot component is a shin, ankle or foot prosthesis.

9. The lower limb prosthesis as claimed in claim 1, wherein the connector is a pyramid connector.

10. The lower limb prosthesis as claimed in claim 1, wherein the piston rod defines an internal cavity.

11. The lower limb prosthesis as claimed in claim 1, wherein the piston rod is a single unitary piece of titanium alloy.

12. The lower limb prosthesis as claimed in claim 1, further comprising an adaptive control system having a flexion control device arranged to resist flexion at a knee joint hydraulically, and an electronic processing circuit electrically coupled to a sensor, and a control device for automatically adjusting the hydraulic resistance to knee flexion according to actions of the user.

13. The lower limb prosthesis as claimed in claim 1, further comprising a micro-processor for controlling knee flexion.

14. The lower limb prosthesis as claimed in claim 1, further comprising at least one valve for flexion and/or extension control.

15. The lower limb prosthesis as claimed in claim 1, further comprising a flexion flow control valve and an extension flow control valve.

16. The lower limb prosthesis as claimed in claim 15, wherein the flexion flow control valve and the extension flow control valve are both controlled by a single actuator, the actuator being controlled by micro-processor control.

17. A lower limb prosthesis, comprising:
   a knee chassis;
   a shin carrier pivotally connected to the knee chassis; and
   a piston and cylinder assembly pivotally connected to the knee chassis and the shin carrier and having a piston and cylinder assembly axis, the piston and cylinder assembly comprising:
      a piston assembly comprising a piston mounted on a piston rod;
      a cylinder body having a cavity defining a cylinder within which the piston is arranged to reciprocate along the piston and cylinder assembly axis; and
      a foot component or a connector for attaching a foot component to the piston and cylinder assembly;
   wherein:
      the knee chassis is pivotally connected to the shin carrier to pivot around a first knee pivot axis (A);
      the knee chassis is pivotally connected to the piston and cylinder assembly to pivot around a second knee pivot axis (C); and
      the shin carrier is pivotally connected to the piston and cylinder assembly to pivot around a distal pivot axis (B), the lower limb prosthesis having a centrode about which the prosthesis rotates, the instantaneous center of rotation being a point where a line passing through the first knee pivot axis (A) and the distal pivot axis (B) intersects a line passing through the second knee pivot axis (C) and which is perpendicular to the piston and cylinder assembly axis, wherein the piston and cylinder assembly, the knee chassis and the shin carrier define a polycentric linkage such that when the piston reciprocates within the cylinder the instantaneous center of rotation of the lower limb prosthesis follows a centrode twice intersecting a line passing through the first knee pivot axis (A) and the second knee pivot axis (C).

18. The lower limb prosthesis as claimed in claim 17, wherein when the piston reciprocates within the cylinder the centrode substantially defines a semi-circle circumference or two thirds of a circle circumference.

19. A lower limb prosthesis, comprising:
a knee chassis;
a shin carrier pivotally connected to the knee chassis; and
a piston and cylinder assembly pivotally connected to the knee chassis and the shin carrier and having a piston and cylinder assembly axis, the piston and cylinder assembly comprising:
  a piston assembly comprising a piston mounted on a piston rod;
  a cylinder body having a cavity defining a cylinder within which the piston is arranged to reciprocate along the piston and cylinder assembly axis; and
  a foot component or a connector for attaching a foot component to the piston and cylinder assembly;
wherein:
  the knee chassis is pivotally connected to the shin carrier to pivot around an anterior knee pivot axis (A);
  the knee chassis is pivotally connected to the piston and cylinder assembly to pivot around a posterior knee pivot axis (C); and
  the shin carrier is pivotally connected to the piston and cylinder assembly to pivot around a distal pivot axis (B),
  wherein the piston and cylinder assembly, the knee chassis and the shin carrier define a polycentric linkage; and
  wherein the piston and cylinder assembly axis and a line passing through the anterior knee pivot axis (A) and the distal pivot axis (B) are substantially parallel as the knee flexes.

20. A lower limb prosthesis, comprising:
a knee chassis;
a shin carrier pivotally connected to the knee chassis; and
a piston and cylinder assembly pivotally connected to the knee chassis and the shin carrier and having a piston and cylinder assembly axis, the piston and cylinder assembly comprising:
  a piston assembly comprising a piston mounted on a piston rod;
  a cylinder body having a cavity defining a cylinder within which the piston is arranged to reciprocate along the piston and cylinder assembly axis; and
  a foot component or a connector for attaching a foot component to the piston and cylinder assembly;
wherein:
  the knee chassis is pivotally connected to the shin carrier to pivot around an anterior knee pivot axis (A);
  the knee chassis is pivotally connected to the piston and cylinder assembly to pivot around a posterior knee pivot axis (C);
  wherein the piston and cylinder assembly, the knee chassis and the shin carrier define a polycentric linkage; and
  the shin carrier is pivotally connected to the piston and cylinder assembly to pivot around a distal pivot axis (B) which lies substantially on the piston and cylinder assembly axis.

* * * * *